United States Patent
Woodside et al.

(10) Patent No.: US 9,062,283 B2
(45) Date of Patent: Jun. 23, 2015

(54) METHOD OF REDUCING CURVATURE IN A MENISCUS OF LIQUID MEDIUM

(75) Inventors: Steven Woodside, Calgary (CA); Jason Dowd, Brampton (CA); Gary Dossantos, Seattle, WA (US); Oliver Egeler, North Vancouver (CA)

(73) Assignee: STEMCELL TECHNOLOGIES INC., Vancouver (CA)

( * ) Notice: Subject to any disclaimer, the term of this patent is extended or adjusted under 35 U.S.C. 154(b) by 496 days.

(21) Appl. No.: 12/528,781

(22) PCT Filed: Feb. 26, 2008

(86) PCT No.: PCT/CA2008/000363
§ 371 (c)(1),
(2), (4) Date: Aug. 26, 2009

(87) PCT Pub. No.: WO2008/104063
PCT Pub. Date: Sep. 4, 2008

(65) Prior Publication Data
US 2010/0047845 A1    Feb. 25, 2010

Related U.S. Application Data

(60) Provisional application No. 60/891,580, filed on Feb. 26, 2007.

(51) Int. Cl.
*C12M 3/00* (2006.01)
*B01L 3/00* (2006.01)
(Continued)

(52) U.S. Cl.
CPC .............. *C12M 23/20* (2013.01); *B01L 3/5085* (2013.01); *C08J 7/047* (2013.01); *C12M 23/10* (2013.01);
(Continued)

(58) Field of Classification Search
CPC .................. B01L 2300/0829; B01L 2300/161; B01L 2300/165
USPC ................................ 435/287.9, 288.3, 288.4
See application file for complete search history.

(56) References Cited

U.S. PATENT DOCUMENTS

| 4,233,029 A | 11/1980 | Columbus |
| 4,303,616 A | 12/1981 | Kano et al. |

(Continued)

FOREIGN PATENT DOCUMENTS

| CA | 2218378 | 8/1997 |
| EP | 1 859 866 | 11/2007 |

(Continued)

OTHER PUBLICATIONS

International Preliminary Report on Patentability, issued on Aug. 26, 2009 in PCT International Application No. PCT/CA2008/000363.
(Continued)

*Primary Examiner* — Nathan Bowers
(74) *Attorney, Agent, or Firm* — Norton Rose Fulbright US LLP

(57) ABSTRACT

The present application is directed to methods of improving cell culture vessel assays. In one aspect the application is directed to a method of reducing the curvature of the meniscus comprising applying a coating material to the interior wall of the vessel, wherein the coating material provides a receding contact angle of about 90 degrees with aqueous solutions and culture media. In another aspect, the application is directed to a method of labeling cells in a first solution by generating droplets of a second solution containing at least one cell-labelling agent and allowing the droplets of the second solution to contact the surface of the first solution.

18 Claims, 13 Drawing Sheets

(51) Int. Cl.
*B01L 3/14* (2006.01)
*C12M 1/00* (2006.01)
*C08J 7/04* (2006.01)
*C12M 1/22* (2006.01)
*C12M 1/32* (2006.01)

(52) U.S. Cl.
CPC ........ *C12M 23/12* (2013.01); *B01L 2300/0654* (2013.01); *B01L 2300/0829* (2013.01); *B01L 2300/161* (2013.01)

(56) References Cited

U.S. PATENT DOCUMENTS

| | | | |
|---|---|---|---|
| 4,426,451 A | 1/1984 | Columbus | |
| 4,741,619 A | 5/1988 | Humphries et al. | 356/246 |
| 4,831,224 A | 5/1989 | Keefer | |
| 5,180,555 A | 1/1993 | Monget | |
| 5,540,891 A | 7/1996 | Portmann et al. | 422/102 |
| 6,074,614 A | 6/2000 | Hafeman et al. | 422/102 |
| 6,730,520 B2* | 5/2004 | Coassin et al. | 436/172 |
| 6,971,530 B2 | 12/2005 | Darr | |
| 6,977,722 B2 | 12/2005 | Wohlstadter et al. | 356/246 |
| 2003/0228705 A1 | 12/2003 | Chan et al. | |
| 2004/0072367 A1 | 4/2004 | Ding et al. | |
| 2004/0082699 A1 | 4/2004 | Brown | |
| 2005/0047971 A1 | 3/2005 | Clements et al. | 156/272.2 |
| 2005/0137355 A1 | 6/2005 | Buckanin et al. | 525/374 |
| 2005/0170498 A1 | 8/2005 | Dolley et al. | 435/288.4 |
| 2005/0226787 A1* | 10/2005 | Shanler | 422/102 |
| 2005/0244838 A1 | 11/2005 | Wojtowicz | |
| 2006/0123893 A1 | 6/2006 | Johans | 73/64.49 |
| 2006/0172412 A1* | 8/2006 | Perrier et al. | 435/297.5 |
| 2007/0110907 A1* | 5/2007 | Brown | 427/393.4 |
| 2007/0154357 A1 | 7/2007 | Szlosek | 422/102 |
| 2007/0274871 A1 | 11/2007 | Jiang | 422/102 |
| 2008/0072964 A1 | 3/2008 | Kim et al. | |
| 2009/0217981 A1 | 9/2009 | Extrand et al. | |

FOREIGN PATENT DOCUMENTS

| | | |
|---|---|---|
| JP | 59088084 A2 | 5/1984 |
| JP | 2008035841 | 2/2008 |
| SU | 1455295 A1 | 1/1989 |
| WO | WO 96/34697 | 11/1996 |
| WO | WO 03/050515 | 6/2003 |

OTHER PUBLICATIONS

Schuderer et al., "Effecy of the Meniscus at the Solid/Liquid Inerface on the SAR Distribution in Petri Dishes and Flasks", Bioelectromagnetics 24, 103-108, 2003.

European Patent Application No. 08714684, Supplementaty European Search Report dated Nov. 22, 2013.

* cited by examiner

METHOD OF REDUCING CURVATURE IN A MENISCUS OF LIQUID MEDIUM

This application is a National Stage of International Application No. PCT/CA2008/000363, filed Feb. 26, 2008, which claims the benefit of Provisional Application No. 60/891,580, filed Feb. 26, 2007, the contents of which are herein incorporated by reference.

FIELD OF THE APPLICATION

This application relates to methods for improving assays performed in culture vessels, for example cell culture plates, including multiwell plates.

BACKGROUND OF THE APPLICATION

Cell-based assays have been used extensively for research and clinical applications. The most commonly used procedure involves the plating, into welled dishes or multi-well plates, of single cell or multi-cell suspensions in liquid or semi-solid nutrient medium, supplemented with the appropriate combinations of ingredients that support the proliferation and, sometimes, differentiation of individual cells. Well dishes and multi-well plates are used for handling a multitude of liquid samples in both chemical and biological studies in fields such as gene sequencing, combinatorial chemistry, drug discovery and proteomics.

Automation of cell-based assays or other assays performed in culture vessels would provide a great improvement to the field and enable high-throughput screening not currently possible with manual assay methods. Key challenges that need to be overcome to facilitate automation of these assays are the development of specific labelling methods and the removal of the optical interference that is a result of meniscus formation where the liquid medium meets the assay dish wall.

U.S. Patent Application publication no. 2007/0274871 describes a well plate of unitary construction comprising a first part of interconnected tubes that define the side walls of each well and a second part defining the wall bases. The hydrophobicity of the first part is selected to have a surface energy that provides a static contact angle of approximately 90 degrees to inhibit meniscus formation.

SUMMARY OF THE APPLICATION

Methods for assays performed in culture vessels, such as multiwell plates, and enabling automation of such assays are described. Improvements encompassed in this application include methods to reduce the optical interference due to meniscus formation when growth medium is placed in a culture vessel, and the labeling of colonies or cells with coloured or fluorescent dyes to ease the classification of cell types by manual or automated methods. It is emphasized that these improvements have wide-ranging applications in the field of biological and chemical sciences. Thus, these improvements apply to all culture vessel and well-plate applications where the absence of a meniscus or labeling of cells is desired.

Several methods and materials are described herein for coating of culture vessels to provide surface properties that will result in a dynamic minimum (receding) contact angle of approximately 90 degrees, and/or increase the mobility of the culture fluid on the surface, in turn resulting in a reduction of meniscus magnitude. The meniscus-reducing properties of the above-described coatings are shown to be robust to prolonged incubation and are effective when used in various vessel and multi-well plate formats.

Accordingly, in one embodiment, the present application relates to a method of reducing the curvature in a meniscus of liquid medium in a culture vessel comprising applying a coating material to interior wall surfaces of the culture vessel, wherein the coating material provides a receding contact angle between the vessel wall and the liquid of about 90 degrees with aqueous solutions and culture media.

In one aspect of the application, the coating material is applied by coating the interior walls of the culture vessel. In a further aspect, the coating material is applied as a preformed material, for example, an insert, into the interior of the culture vessel.

The present application also includes a vessel for holding liquid comprising a coating material on the interior wall of the vessel, wherein the coating material provides a receding contact angle between the interior vessel wall and the liquid of about 90 degrees. The coating materials are applied in a manner and amount effective to reduce the curvature in the meniscus of cell culture medium.

The present application also includes uses of the vessels of the present application for culturing cells or for performing imaging-based assays. The present application further includes a method of imaging cells comprising culturing the cells in a cell culture medium in a vessel of the present application and imaging the cells.

Methods are also presented herein for the application of labeling agents to the surface of culture vessels with minimal disturbance to the cells or other materials suspended in medium. The labeling agents Neutral Red and a fluorescently labelled antibody to a cell surface marker were aerosolized using a nebuliser or airbrush nozzle and the aerosol was directed onto the culture surface. These methods were shown to enhance the contrast of cells by brightfield microscopy and fluorescence microscopy, and to distinguish cell types by detection of fluorescence of bound label. Since the classification of cells by visual observation of morphological characteristics is a laborious and subjective process that further contributes to the variability of the assay, the described labeling method presents a potential for reducing the assay variability and enabling automation of the quantification and classification of cells or cell colonies.

Accordingly in another of its aspects, the present application includes a method to label cells in a first solution by generating droplets of a second solution containing at least one cell-labelling agent and allowing the droplets of the second solution to contact the surface of the first solution.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DETAILED DESCRIPTION OF THE APPLICATION

Figure 1:
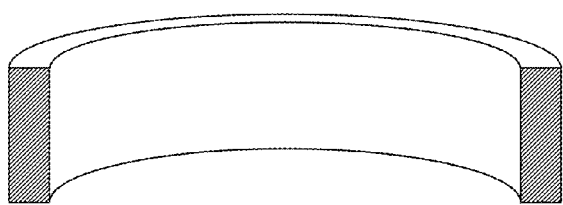
FIG. 1 is a depiction of an UHMW well insert used for meniscus reduction according to one embodiment of the present application. The drawing represents a lateral cross-section of the cylindrical insert.

When a liquid is placed adjacent to a vertical wall, the liquid/vapour surface assumes a shape that is characteristic of the physiochemical properties of the three phases involved (solid, liquid and vapour phase). The angle defined by the liquid and solid surfaces at the point of contact of the three phases is termed the "contact angle" (θ). The magnitude of this angle is determined by the interfacial free energies (surface tension, γ) of the liquid-vapour (LV) interface, the liquid-solid (LS) interface, and the solid-vapour (SV) interface. For an ideal, homogenous surface, the magnitude of the contact angle is given by Young's equation:

$$\gamma_{LV}\cos\theta = \gamma_{SV} - \gamma_{SL} \quad (1)$$

For the purposes of the present application, the liquid phase is considered to be an aqueous solution, in particular viscous aqueous solutions comprising biopolymers such as proteins, peptides and polysaccharides, or cell culture media. When contained by vertical solid surfaces on all sides, the LV interface assumes a curved shape dependent on the magnitude of the contact angle. This shape of the surface is commonly termed the "meniscus" of the liquid phase. A marked meniscus is often formed along the top surface of common solutions in biological sciences. Due to the contact angle properties defined above, surface energies of the solution and the containing solid interfaces are often cited as defining properties that determine meniscus shape and magnitude. However, physiochemical properties, in addition to surface energies of the liquid and solid surfaces, are of importance in determining meniscus shape of aqueous liquids at equilibrium. Such properties include (a) the three-dimensional topology of the solid surface, (b) the composition of the liquid phase, (c) physical and chemical heterogeneity of the solid surface, and (d) inducibility of configurational changes of the solid surface by the liquid.

Properties c and d above effect an influence on meniscus shape by causing contact angle hysteresis, defined as the discrepancy between the maximum and minimum contact angles observed for a liquid drop when the point of contact of the liquid, solid, and vapour phases is advanced and retreated across the solid surface. Briefly, when the liquid advances over the solid surface, the contact angle is observed to be greater than when the liquid retreats from the solid surface. These "advancing" and "receding" contact angles are taken as the dynamic maximum and dynamic minimum contact angles, respectively, and their difference is referred to as the contact angle hysteresis. This hysteresis is caused by the energies required to overcome the heterogeneity in hydrophobic and hydrophilic domains on the surface (chemical heterogeneity), or overcome physical barriers on the solid surface (physical heterogeneity, or surface "roughness").

In the case of chemical heterogeneity, as an aqueous solution advances over a surface, hydrophobic domains on the surface will impede the motion of the solution and result in an increase in contact angle, whereas as the solution recedes from the surface, hydrophilic domains on the surface will retain the liquid on the surface, resulting in an increase in contact angle.

In the case of physical heterogeneity, microscopic variations in the surface will impede the motion of the solution providing resistance to the advancing front of the liquid (thus increasing contact angle), and hold back the receding boundary of the liquid-solid surface as the liquid recedes (thus decreasing contact angle).

Configuration changes of the solid surface brought on by contact with the liquid phase introduces additional hysteresis into observed contact angles. The change in surface configuration is a result of the reorientation of functional groups on a polymeric solid surface when exposed to the liquid in order to minimize interfacial tension at the surface between the solid and liquid phases. This reorientation is thought to consist primarily of a rotation of the surface functional groups about the molecular axis, rather than a rearrangement of the macromolecular structure of the polymer. The result is that portions of the solid surface that have been exposed to the liquid phase (ie. have been "wetted") will exhibit an altered surface energy. In the case of aqueous liquids in contact with the surface of a solid hydrophobic polymer, the wetted surface is expected to exhibit a reduced hydrophobicity compared non-wetted surfaces, due to rotation of hydrophobic moieties away from the surface. Thus, when the liquid phase recedes over a wetted surface, a reduced contact angle results compared to the static contact angle of the liquid on a non-wetted surfaces. This further contributes to the altered magnitude of a receding contact angle.

Composition of the aqueous solution is likely to affect contact angle hysteresis. For example, presence of components that modulate the hydrophobic and hydrophilic interactions between the liquid and solid surfaces, or alter the surface energies of the liquid-vapour and liquid-solid interfaces are likely to affect the hysteresis. The presence of molecules with polar and non-polar regions, such as surfactants, phospholipids, or fatty acids, may be expected to modulate interactions between hydrophobic and hydrophilic moieties on the solid surface and the aqueous liquid. Such molecules may also exert varying effects on the configuration of the surface functional groups of the solid phase, further altering contact angle. Furthermore, solubilized components may adhere to the solid surface, altering its surface energy and affecting the contact angle. For example, albumin-containing solutions have been shown to affect contact angles of the solution with hydrophobic surfaces due to protein adsorption to the surface. In addition, composition of the aqueous solution may affect the viscosity of the liquid and hence the energy required to return the system to its equilibrium state after a physical disturbance (i.e. highly viscous solutions result in altered contact angles at equilibrium, compared to similar solutions of lower viscosity).

Advancing and receding contact angles are commonly determined by one of two methods: (1) The sessile drop method whereby a drop of the liquid phase is placed on the solid surface. In this case, the advancing angle is obtained by addition of volume to the drop and a receding angle is obtained by removal of volume from the drop. (2) The Wilhelmy plate method, whereby a polymeric surface is slowly immersed in the liquid phase (resulting in the advancing contact angle) and then withdrawn from the surface (resulting in the receding contact angle). These methods result in different absolute contact angles, due the sessile drop method having a stationary horizontal surface, and the Wilhelmy plate method having a moving vertical surface.

For the purpose of clarity, meniscus formation of a liquid will be discussed in a cylindrical tube, although the above mentioned aspects of contact angle and meniscus apply to containers of a variety of shapes (eg. square, round, or triangular tubing, wells, or other containers). When an aqueous solution is placed in a hydrophobic cylinder, the shape of the meniscus is dictated by the advancing contact angle as the level of the liquid rises within the cylinder. For an ideal homogenous surface, when addition of the liquid is complete, the shape of the meniscus will come to equilibrium as dictated by the intrinsic contact angle of the system as defined by Young's equation. However, in real-world applications, ideal homogenous surfaces are unlikely. As such, contact angle hysteresis will come into play if the system is not completely static. Any physical disturbance of the container, such as vibration, rotation, or acceleration/deceleration due to movement of the container will result in movement of the liquid level and the three-phase contact line (ie. the intersection of the solid, liquid, and vapour phases) will be subjected to a cycle of advancing and receding contact angles. Following such a cycle, a new equilibrium contact angle is established, not represented by Young's ideal contact angle, but by the receding contact angle on the wetted surface. Currently, there is no universal theory which accurately models this contact angle in complex systems, and thus the receding contact angle and the resulting meniscus is best determined empirically for different systems (see examples hereinbelow).

In summary, in a completely static system for typical aqueous solutions contained by solid surfaces, the meniscus shape is defined by the intrinsic contact angle as predicted by Young's equation. However, such static systems are essentially never encountered in routine laboratory tasks, especially since procedures involving solutions commonly require physical mixing after addition to a container. In the more common scenario, where the liquid surface is subject to physical disturbance, the meniscus shape is sensitive to contact angle hysteresis, topology of the interior wall surface of the container, and composition of the aqueous solution. It is proposed that the receding contact angle of the system is the primary indicator of meniscus shape and magnitude. Consequently, while an intrinsic contact angle of 90 degrees will be characteristic of perfectly flat meniscus in a completely static system, a receding contact angle of 90 degrees is required to maintain a flat meniscus in a system subject to physical disturbance, as commonly encountered in most real-world applications.

One limitation of current assay vessels and well-plates is that the meniscus on the medium at the circumference of the dish or well causes optical distortion around the circumference of the plate. In this area it is more challenging to see the cells or colonies using a visible light microscope in visible light transmission or darkfield mode or in fluorescent mode. Images acquired using a camera and static optics, or using moving optics such as in a scanner, show the meniscus effect. The pattern recognition ability of the human brain can handle the varying background and human observers are able to identify the entities in the images or under a microscope. However, it is easier to identify the entities where there is no meniscus. In addition, computer-based image analysis is much more challenging when the background is variable because common approaches use the difference in intensity or brightness between the background and foreground to distinguish objects. Thus there is an advantage to eliminating optical interference due to the meniscus for both manual and automated imaging of cells and other entities in culture wells or culture vessels. This advantage would extend to any assay where optical or spectroscopic measurements or observances are made, including for example, fluorescence-, UV light-, infrared light- and visible light-based assays.

It has been shown that if the vertical walls of a culture vessel exhibit surface energies that result in an intrinsic contact angle of approximately 90 degrees, the magnitude of the meniscus of the culture media is minimized, which in turn reduces the dark rim generally seen around the edge of the culture vessel. Furthermore, it has been shown that physical disturbance to common aqueous solutions and culture media within the culture vessel results in formation of a meniscus. This is due to contact angle hysteresis commonly exhibited with interfaces of aqueous solutions and solid surfaces. Another effect of reducing the meniscus at the edge of a culture vessel is that the medium, and any cells suspended in the medium, is more evenly distributed throughout the vessel. For example, with CFC assays in semisolid media (e.g. Clonacell™ or MethoCult™) the colonies distributed evenly throughout the medium. However, the meniscus increases the thickness of the medium in the area near the well or dish wall, giving an apparent higher concentration of cells and colonies near the wall when the cells are viewed from the top or bottom. This higher concentration near the wall also increases the difficulty of identifying cells and colonies by different imaging modes.

It has also been shown that if the walls of culture vessels are treated so as to provide a receding contact angle of about 90 degrees, the meniscus reducing features of the surfaces are robust to physical disturbance and prolonged incubation. This improves the ability of manual operators and automated systems to distinguish entities near the rim of the culture vessel.

Accordingly, in one embodiment, the present application relates to a method of reducing curvature in a meniscus of liquid medium in a culture vessel comprising applying a coating material to interior wall surfaces of the culture vessel, wherein the coating material provides a receding contact angle between the vessel wall and the liquid of about 90 degrees with aqueous solutions and culture media.

In an embodiment of the present application the coating material provides a receding contact angle of about 75 degrees to about 110 degrees, about 80 degrees to about 110 degrees, suitably about 85 degrees to about 105 degrees, with aqueous solutions and culture media. In an embodiment, the receding contact angle is also known as the dynamic receding contact angle. In an embodiment of the application, the coating material inhibits adhesion of molecular constituents present in aqueous solution or cell culture medium, so as to prevent alteration of the surface properties of the coating.

The "interior wall surfaces" of the vessel refer to at least the area on the side walls of the vessel that come into contact with the liquid, in particular the leading edge of the liquid where a meniscus is formed. The entire surface area of the vessel may also be coated with the coating material.

The coating material can be applied to the vessel wall by any suitable method, for example, using a method selected from:

Application or insertion of pre-formed materials (with or without adhesive);

Application of the material using a physical applicator followed by removal of excess material;

Application by immersion of the vessel into the coating material or a solution thereof, followed by drying;

Application of a melted material followed by cooling and solidification;

Dissolution of the coating material in a suitable solvent and application of this solution, followed by removal of the solvent through evaporation, aspiration, and/or washing;

Application of a material that cures upon exposure to air; and

Application of an agent following addition of the material that causes the material to cure.

Alternatively, the culture vessel could be made partly or entirely of the coating materials if the material being used is sufficiently rigid.

By "physical applicator", it is meant any device that can be used to apply the coating material to the vessel. For example, the physical applicator may be a lint-free material, such as a lint-free tissue, which may be used on its own or attached to a suitable applicator device.

Once the material is applied, it may be allowed to set for a sufficient period of time, access may be removed if necessary (for example using a clean physical applicator) and the material allowed to cure, for example by incubating for a suitable time and temperature. A person skilled in the art would be able to determine curing conditions based on the vessel type and identity of the coating material. For example polystyrene vessels may be incubated at a temperature of about 50° C. to 100° C., where PTFE vessels may be incubated at higher temperatures, for example about 150° C. to about 250° C. Vessels are cooled to room temperature prior to use.

The time between applying the coating material and using the vessel will depend on the application method. Vessels prepared with materials that are pre-formed can be used immediately. Vessels prepared with materials that require removal of a solvent or curing will require anywhere from a few minutes to several days depending on the material, the application method and the atmospheric conditions as would be known to a person skilled in the art.

In an embodiment of the application, the preformed coating materials are fabricated as inserts to fit the internal diameter of the vessel. In a further embodiment, the inserts are made of any suitably durable, non-reactive material. In a further embodiment the preformed materials are coated with a hydrophobic material that results in a receding contact angle of approximately 90 degrees with common aqueous solutions and culture media.

The coating material is any material that can be made to adhere to the culture vessel to result in a dynamic minimum (receding) contact angle of about 90 degrees with common aqueous solutions and culture media. Potential coating materials include, without limitation, one or more of the following:

liquid siliconizing agents such as solutions of methylsiloxanes, methylvinylsiloxanes, and methyl-perfluorobutylethylsiloxanes and their copolymers;

fluoropolymer agents, including fluoropolymer solutions in low boiling point fluorosolvents;

paraffin waxes;

polyolefin waxes;

animal and insect waxes, including beeswax, shellac, spermaceti, lanolin;

vegetable waxes, including bayberry, candelilla, carnauba, castor, esparto, Japan, jojoba oil, ouricury, and rice bran;

mineral waxes, including ceresin, montan, ozocerite, and peat;

wax-like saturated fatty acids, including lauric, myristic, palmitic, margaric, stearic, arachidic, behenic, tetracosanic, lignoceric, cerotic, and melissic acid;

non-wax-like saturated fatty acids, including butyric, caproic, caprylic, and capric acid;

wax-like unsaturated fatty acids, including tiglic, hypogaeic, gaidic, physetoleic, elaidic, isooleic, erudic, brassidic, and isoerudic acids;

non-wax-like unsaturated fatty acids, including oleic, linoleic, alpha-linoleic, arachidonic, eicosapentaenoic, docosahexaenoic, and erucic acids;

wax-like fatty alcohols, including 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tricosanol, 1-tetracosanol, 1-pentacosanol, 1-hexacosanol, 1-heptacosanol, 1-octasanol, 1-nonacosanol, 1-tricontanol, 1-hentriacontanol, 1-dotriacontanol, 1-tritriacontanol, and 1-tetratriacontanol;

non-wax-like fatty alcohols, including 1-hexanol, 1-heptanol, 1-octanol, 1-nonanol, 1-decanol, 1-undecanol, 1-dodecanol, and 1-tridecanol;

solid materials, including materials comprising copolymers of hexafluoropropylene (HFP) and vinylidene fluoride (VDF or VF2), terpolymers of pertetrafluoroethylene (PTFE) or tetrafluoroethylene (TFE), vinylidene fluoride (VDF) and hexafluoropropylene (HFP) as well as perfluoromethylvinylether (PMVE), silicon (available commercially as Viton™ from Dupont Performance Elastomers); Buna Nitrile (also called standard grade nitrile), fluorosilicon, neoprene, urethane, HSN (Highly Saturated Nitrile), silicone rubbers, and ethylene propylene diene monomer (EPDM).

Also included are various esters of the above-listed fatty acids with any suitable fatty alcohols, or sterols such as cholesterol, or glycerols.

In a suitable embodiment, the coating material is silicone based, fluoropolymer based, petroleum jelly, paraffin wax, EPDM or Buna Nitrile or is an insert that is made of silicone, EPDM or Buna Nitrile or that is coated with a coating material that is silicone based, fluoropolymer based, petroleum jelly, paraffin wax, EPDM or Buna Nitrile. In a further suitable embodiment the silicone-based material comprises non-crosslinked siloxane, methylsiloxane or methylvinyl siloxane or copolymers thereof.

The method of the present application is in particular applicable to viscous aqueous solutions or gels. By viscous it is meant that the solution has a viscosity or resistance to flow that is greater than the viscosity of water, or greater than about 1 mPa·s, suitable greater than about 5 mPa·s, and up to about 4000 mPA·s. In an embodiment of the application, the viscous aqueous solution is any such solution commonly used in cell culture or cell-based assays, for example, biological buffers and any medium that can support the growth of cells, including without limitation, Iscove's modified Eagle's Medium (IMDM), Dulbecco's modified Eagle's Medium (DMEM), Hank's balanced salt solution, methycellulose-based media (such as MethoCult™), agar-based media, gelatine-based media and collagen-based media. In a further embodiment of the application, the viscous aqueous solution is a solution comprising biopolymers, such as proteins, glycoproteins, peptides, polysaccharides and/or oligonucleotides and/or water soluble polymers such as polyalkylene glycols. In yet another embodiment of the application, the solution is one that comprises molecules that alter the surface properties of the interior walls of the vessels, thereby altering the contact angle of the walls when the walls are wetted with the solution.

The present application also includes culture vessels, such as cell culture vessels, for holding liquid with a material coated thereon, wherein the coating material provides a receding contact angle between the vessel wall and the liquid of about 90 degrees. The culture vessel can be any vessel including, without limitation, culture dishes or wells of multiwell plates. In an embodiment of the application the vessel is made from polystyrene, polytetrafluoroethylene (PTFE), polypropylene, polycarbonate, polyvinylchloride, or other similar solid polymeric substrate.

The coating materials are applied in a manner and amount effective to reduce the curvature in the meniscus of cell culture medium or other common aqueous solutions by resulting in a surface energy to enable a receding contact angle of about 90 degrees, suitably about 75 degrees to about 110 degrees, more suitably about 80 degrees to about 110 degrees, even more suitably about 85 degrees to about 105 degrees. In an embodiment the receding contact angle is also known as the dynamic receding contact angle.

The present application also includes uses of the vessels of the present application for culturing cells or for performing imaging-based assays. Imaging-based assays may be any such assay used in both the biological and chemical arts, for example, colony forming cell (CFC) assays, gene sequencing, combinatorial chemistry, drug discovery and proteomics.

The present application further includes a method of imaging cells comprising culturing the cells in a cell culture medium in a vessel of the present application and imaging the cells.

In an embodiment of the application, the imaging of the cells or imaging-based assay is performed using visible light, ultraviolet light, infrared light and/or fluorescence, in particular visible light. Visible light imaging may be performed, for example, using darkfield mode, brightfield mode, phase contrast or differential interference contrast. In a further embodiment the imaging in done manually or automatically. In another embodiment of the application, the cells being imaged are in a cell colony.

The 3-dimensional distribution of cells in a semi-solid medium makes it difficult to add reagents to the culture without disturbing the cells. For example, to improve the contrast of cells relative to background for fluorescence or visible light microscopy it may be beneficial to add a stain that labels cells. Typically, stains used with viable cells are added to liquid suspension cultures with a pipette. This is not acceptable for a cell assay in semi-solid media such as MethoCult™ or ClonaCell™ (Stemcell Technologies Inc) because the cells will be disturbed or disrupted by the convective flow at the point of addition. The stain will also be localized in a medium where the stain must be distributed throughout the culture only by diffusion since there is little if any convective flow within the 1% methylcellulose solution used in this assay. In standard liquid suspension cultures convective mixing is more import than diffusion for evenly distributing a labelling reagent. Consequently, there is a need in the art to improve a method of adding stain to a semi-solid culture media.

It has been shown that by aerosolizing a cell staining agent, it is distributed more evenly and at a slower rate than when added the usual way with a pipette. This is advantageous as the cells are stained without disturbing their morphology.

Accordingly, in another embodiment, the present application provides a method to label cells in a first solution by generating droplets of a second solution containing at least one cell-labelling agent and allowing the droplets of the second solution to contact the surface of the first solution. Methods that produce fine droplets that settle onto the surface of the medium will have the potential to distribute liquid evenly over the surface of media in wells or dishes without disrupting cell colonies in the media.

The cell-labelling agent can be any compound that interacts with the cells to create a change in the contrast of the cell with the background. For example the cell labelling agent can be a visible light dye that binds to a cellular component or a conjugated antibody that binds to a specific cell-surface antigen or a compound that reacts with a cellular component and can be detected by visible light or fluorescence.

The visible light dye can be any dye that absorbs in the visible spectrum and changes the color of cells when bound to the cells. Examples of some dyes include, without limitation, neutral red, Bismarck brown and Nile blue.

Examples of some fluorescent entities that can be conjugated to antibodies include, without limitation, fluorescein, tetramethylrhodamine isothiocyanate, phycoerythrin, peridinin-chlorophyll-protein complex (PerCP), Cy3, Cy5, C5.5, Cy7, Texas Red, Alexa 488, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700 and Alexa Fluor 750 and quantum dots.

Examples of compounds that react with a cellular component include, without limitation, tetrazolium compounds such as (3-(4,5-Dimethylthiazol-2-yl)-2,5-diphenyltetrazolium bromide (Yellow MTT), MitoTracker Green FM, MitoTracker Deep Red 633, Hoechst 33342, calcein AM, calcein red-orange AM, Lavacell (Active Motif, CA), Cell Trace™ BODIPY® TR methyl ester, LysoTracker Red DND-99, The first solution containing cells is a viscous liquid or a gel that contains, without limitation, methylcellulose, agar, gelatin or collagen as a component of the cell culture medium.

The cell culture medium can be any medium that can support the growth of cells including, without limitation, Iscove's modified Eagle's Medium (IMDM), Dulbecco's modified Eagle's Medium (DMEM) and Hank's balanced salt solution.

The droplets can be generated using techniques known in the art, including aerosol droplets that are prepared using a nebuliser or using ink jet technology. A nebuliser produces an aerosol from a liquid using the Venturi effect. When an aerosol is produced over the surface of the medium, some fraction of the aerosol droplets settle onto the surface of the culture. Another common consumer product that produces an aerosol is an airbrush. Airbrushes typically use the Venturi effect too, producing an aerosol carried in an air stream. An inkjet printer produces fine droplets of ink using different mechanisms that do not require air flow and is another potential means to deliver liquid evenly to the surface of semi-solid media without disrupting colonies. Airless spray nozzles will also generate an aerosol.

The methods of the present application are particularly applicable to colony forming cell (CFC) assays. Since their introduction more than 30 years ago, hematopoietic CFC assays have been used extensively for research and clinical applications to quantify multi-potential progenitors and single lineage-restricted progenitors of the erythroid, granulocytic, monocyte-macrophage and megakaryocytic pathways. The most commonly used procedure involves the plating into dishes or multi-well plates of a single cell suspension in semi-solid nutrient medium, supplemented with the appropriate combinations of cytokines, that supports the proliferation and differentiation of individual progenitor cells into discrete colonies containing recognizable progeny. The CFCs are classified and enumerated based on morphologic recognition of mature cells within the colony in situ by light microscopy. The number of colonies obtained should be linearly proportional to CFC content of the input cell suspension provided that a sufficiently low number of cells are plated. In general, under 'optimal' assay conditions, colonies containing cells of two or more lineages (mixed colonies) arise from a more primitive progenitor than those containing cells of a single lineage. More immature progenitors generate larger colonies and require a longer period of time in culture to allow maturation of the cells within the colony.

There are numerous applications for the CFC assay. It is used to measure progenitor cell numbers in the development of stem cell enrichment strategies and other ex vivo manipulations, to identify stimulatory and inhibitory growth factors and to evaluate the hematopoietic proliferative potential of bone marrow, cord blood and mobilized peripheral blood samples for transplantation. Because the assay is the benchmark functional assay to assess the ability of various hematopoietic cell types to divide and differentiate, it has been the especially useful for evaluating the effects of ex vivo manipulations including T cell depletion, HSC and progenitor cell enrichment, gene therapy and cryopreservation, on the quality of hematopoietic grafts. The CFC assay is also used to monitor hematopoietic engraftment after transplantation and to test the potential hematotoxicity of novel therapeutic agents. In its current format, the CFC assay is the accepted assay for determining the progenitor content of grafts at cord blood banks and other cell processing laboratories.

Applied to toxicology testing during drug development, colony forming cell assays are more reliable and informative than assays that measure effects on proliferation, metabolism or survival of continuous cell lines. The culture of progenitor cells for 1 to 2 weeks allows proliferation into colonies, giving insight into the kinetics of growth and making them a more sensitive assay than those measuring only cell death. In addition, multiple progenitor cell types can be cultured allowing the detection of lineage specificity and identification of specific target populations.

Cells from different animal species may be used, allowing one to highlight potential differences between humans and preclinical test species. Before performing in vivo studies, mouse or rat cells can be used to refine doses and reduce the number of animals required for preclinical toxicology. Human cells can be used to determine the accuracy of extrapolating human data from an animal model. As such, it is possible to reduce the uncertainty of the starting dose in phase I clinical trials and treat fewer patients with ineffective doses. These assays provide the opportunity to bridge the gap between animal models and clinical trials.

A current limitation to CFC assays is the requirement for subjective classification and quantification of colonies. This is a time consuming, variable process and costly in terms of personnel hours. Automation of such assays would provide a great improvement to the field and enable high-throughput screening not currently possible with the manual assay method. Key challenges that need to be overcome to allow automation of this assay are the development of specific labelling methods of colony classes, and the removal of the optical interference that is a result of meniscus formation where the culture medium meets the assay dish wall. These problems are addressed by the methods of the present application.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of the present application:

EXAMPLES

Example 1

"Wipe-on"/"Wipe-off" Application of Coating Agents to Surfaces

This method was employed for treating polystyrene culture surfaces (Greiner 657102 and 627102) and PTFE surfaces (Teflon™) with various agents such as siliconizing agents (Syl-off™ (Dow Corning Q2-7785), Aquasil™ (Pierce 42799) and Surfasil™ (Pierce 42800)), fluoropolymer agents (Fluoropel™ coatings, Cytonix corp.), and common petroleum jelly (white petrolatum, USP). The agents were applied as follows:

A lint free tissue was wetted with the agent and was wiped firmly over the culture surface, creating a thick film of the agent on the surface ("Wipe-on").

The film was left for a period up to 60 min at ambient conditions (18 to 25° C., 50 to 70% relative humidity (RH)) and then excess agent was removed by gently rubbing the surface in a smooth motion, using a clean lint-free tissue. This "wipe-off" step left a thin film of the agent, faintly visible by eye.

The treated surfaces were incubated for 30 to 120 min at 60 to 85° C. for polystyrene materials, or 190 to 210° C. for PTFE surfaces. Treated surfaces were cooled to ambient conditions prior to assessment of coating properties.

Properties considered for assessment of coatings were maximum and minimum (as determined from advancing and receding) contact angles, as well as the intrinsic static contact angle (considered to be the mean of the advancing and receding contact angles), mobility of the fluid on the coated surface, meniscus width, and optical interference as a result of meniscus formation.

Example 2

Immersion Method of Application of Coating Agents

PTFE or polystyrene surfaces were treated siliconizing agents (Sigmacote™ (Sigma SL2)) or fluoropolymer agents (Fluoropel™ coatings, Cytonix corp.) by the immersion method as follows:

The agent was placed in a suitably sized glass container. Alternatively, if the surface of a dish or container was to be coated, the agent was placed directly in the dish or container.

The surface to be coated was fully immersed in the coating agent.

The surface was removed from the agent (or the agent from the surface in the case of a dish or container) and oriented so as to allow the excess agent to flow from the surface.

The solvent was allowed to dry by evaporation at ambient conditions. Alternatively, the agent may cover the surface better by lightly wiping the surface with a non-absorbent material (eg. Latex glove) prior to air drying.

The treated surfaces were incubated at 60 to 85° C. for a period of 30 min.

Example 3

Construction of Physical Wall Features in Polystyrene Culture Wells

Well inserts exhibiting a smooth vertical surface were fashioned from silicon, EPDM, and Buna Nitrile. The external diameter of the inserts resulted in a firm fit to the well wall surface when inserted into 6-well polystyrene multiwell plates (FIG. 1).

Example 4

Measurement of Contact Angle of Liquid Drops with Different Surfaces

In order to quantify contact angles at the three-phase (solid substrate-aqueous liquid-air) contact line, a 20 µL droplet of the liquid was slowly placed onto the surface. Lateral view images of the droplet resting on the surface were captured with the use of a Lumenera digital camera and a 0.6× magnification lens. The lens was oriented horizontally facing the drop, at a level even with the solid surface. Illumination was provided by backlighting with an amber LED behind an opaque diffuser. Image capture conditions were maintained at constant settings (Gain 1, exp. 0.3 s, acquisition resolution 2080×1536). Advancing contact angles were determined by image capture within 2 to 5 s of drop placement (upon completion of slow addition of volume to the droplet to advance the contact line over the surface). Receding contact angles were determined by image capture after increasing the droplet volume to 40 µL and then removal of 20 µL to recede the contact line over the surface. Images were again captured within 2 to 5 s of droplet manipulation.

Figure 2:
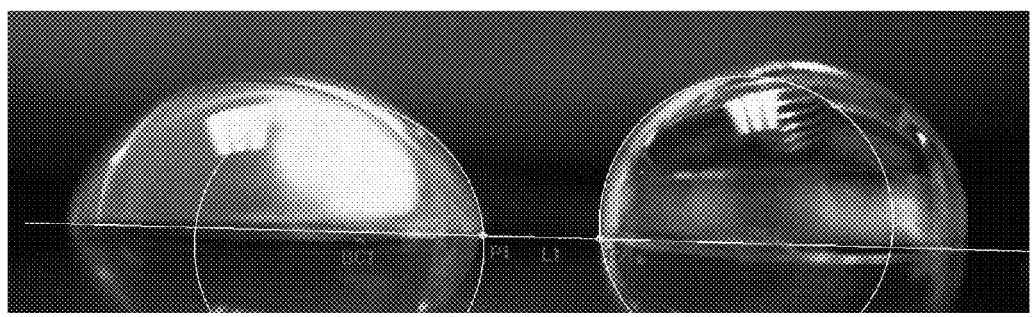
FIG. 2 is an image of droplets of approximately 20 µL of MethoCult (left) and water (right) on a flat polystyrene surface. Approximations of the curvature of the droplet surface at the interface with the solid substrate are shown as circles with centers BC1 and BC2. The plane of the polystyrene surface is shown by the line L2. Points of contact of the liquid to surface are indicated by P1 and P2. The contact angle is calculated as the angle between the tangents to the circles at points P1 and P2 and the plane of the substrate, L2.

The contact angle was determined by analysis of lateral view images. Briefly, the horizontal plane (droplet baseline) of the image was established by drawing a straight line (L1) through the contact points of the droplets with the substrate (FIG. 2). A best fit circle (BC1) is drawn through perimeter points of the droplet near the contact points of the left and right margins of the droplet with the surface. This curve is intended to be a best fit to the curvature of the droplet near the contact point. A reference point (P1) is placed at the intersection of L1 and BC1. The angle between L1 and the tangent to the curve at P1 is taken to be the contact angle.

The static contact angle was calculated as the average of the advancing and receding contact angles. The dynamic minimum contact angle was taken to be the receding contact angle.

Example 5

Measurement of Surface Mobility

Surface mobility was determined qualitatively by the degree of change of the contact diameter of a 20 µL liquid drop placed on a surface and subjected to dynamic volume change by addition (advancing contact line) and removal (receding contact line) of a 20 µL volume of the liquid. The contact diameter was determined from lateral images acquired as described in Example 4, and measurement of the distance between left and right contact points of the droplet with the surface. The percent change in diameter between advancing and receding droplets was calculated. A return to the original droplet diameter after a receding volume is indicative of a high surface mobility. Therefore, the % change in diameter is inversely related to surface mobility.

Example 6

Measurement of Meniscus Width and Height

Figure 3:
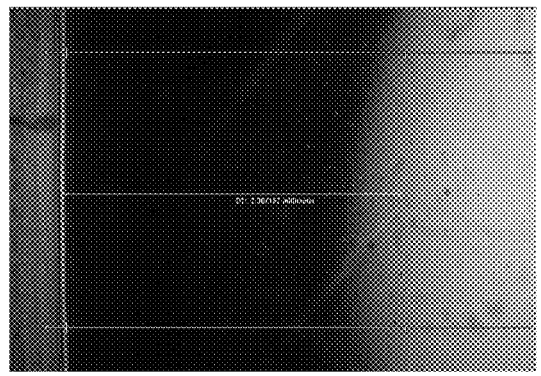
FIG. 3 is a brightfield, phase-contrast image of the interface of the wall of a 35 mm culture dish and the semisolid culture medium present in the dish. The image was acquired using an inverted microscope with a 2.5× objective lens. The darkened area extending from the dish wall (on left) towards the center of the dish demonstrates the optical interference introduced by the meniscus. The measurement line is the estimation of meniscus width from the image following spatial calibration of the image. The horizontal lines at the top and bottom of the image delineate the area used for calculation of optical interference.

Meniscus width was determined by acquiring brightfield images of the liquid surface of test solutions at the interface with the silicone coated walls of the culture dishes (see FIG. 3, for example of an untreated well exhibiting a meniscus). The images were acquired using an inverted microscope (Zeiss Axiovert™ 40 CFL) and a Fuji Finepix™ S2 digital camera through a 2.5× magnification objective and 2.5× camera ocular. The width of the meniscus was determined by spatial calibration of these images and measurement of the dark area using digital image processing methods.

Meniscus height was determined by capturing side profile images of culture dishes to visualize the lateral meniscus. Images of culture dishes placed in front of a black background were acquired using a Canon Powershot™ A75 camera. The height of the visible meniscus was determined by spatial calibration of these images and measurement of meniscus vertical dimensions using digital image processing methods.

Example 7

Measurement of Meniscus Optical Interference for Microscopy with Different Surfaces Optical interference resulting from the meniscus was quantified by integration of the intensity profile of the dark area corrected for image brightness using images acquired as in Example 4. Optical interference is stated as a percentage normalized to the integrated pixel intensity values obtained for the meniscus formed by 1% methylcellulose/IMDM in an untreated polystyrene dish.

Example 8

Effect of Silicone Surface Treatment on Advancing Contact Angle

Polystyrene surfaces were treated with Surfasil™ and Syl-off™ as described in Example 1. In addition, polystyrene and PTFE (Teflon™) surfaces were treated with Sigmacote™ as described in Example 2. The advancing contact angles of surfaces after siliconizing treatments were measured as described in Example 4 and the results are summarized in Table 1.

Contact angles of surfaces with water were generally greater than with Methocult™, with the exception of untreated PTFE, for which the contact angles were similar for both fluids. Sigmacote™ treatment did not appreciably change the contact angles of polystyrene with Methocult™ or water; however, treatment of PTFE with Sigmacote™ did substantially lower the contact angles for both Methocult™ and water. Surfasil™ substantially decreased the contact angle of polystyrene with Methocult™ and water, whereas Syl-off™ substantially increased the contact angles of polystyrene with both fluids.

Example 9

Effects of Silicone Surface Treatments on Meniscus Magnitude

Polystyrene surfaces were treated with Aquasil™, Surfasil™ and Syl-off™ as described in Example 1. In addition, polystyrene and PTFE (Teflon™) surfaces were treated with Sigmacote™ as described in Example 2. MethoCult™ semi-solid medium (StemCell Technologies, Vancouver, Canada) was added to the coated culture dishes and spread throughout the dish by tilting and rotating of the dishes, resulting in dynamic meniscus formation. Dishes were incubated for varying periods of 1 to 10 days at 37° C. in a humidified incubator. The effects of siliconizing treatments on meniscus width, height, and optical interference (collectively, the meniscus magnitude) were measured as described in Examples 6 and 7. The results are summarized in Table 1 and Table 2.

Applying a silicone coating to PTFE using Sigmacote™ significantly reduced the observed meniscus, while untreated PTFE did not exhibit a reduction in meniscus magnitude as compared to untreated polystyrene controls.

Figure 4:
FIG. 4 is an image of the dish wall/culture medium interface of an Aquasil coated dish acquired within 24 hrs of placement of medium into the dish. The marked reduction in meniscus magnitude is evident.
Figure 5:
FIG. 5 is an image of the dish wall/culture medium interface of a Sigmacote™ coated dish acquired within 24 hrs of placement of medium into the dish. The meniscus is visible as a thin dark band adjacent to the dish wall.
Figure 6:
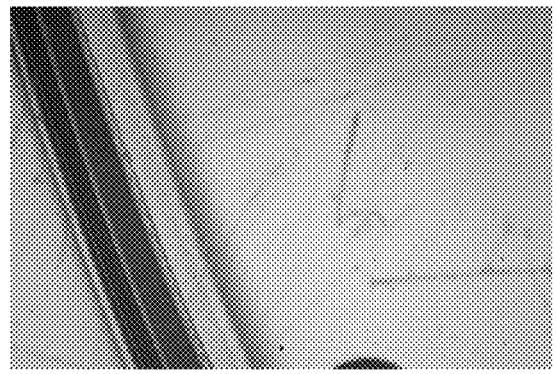
FIG. 6 is an image of the dish wall/culture medium interface of a Syl-off™ coated dish acquired within 24 hrs of placement of medium into the dish. The marked reduction in meniscus magnitude is evident.
Figure 7:
FIG. 7 is an image of the dish wall/culture medium interface of a Surfasil™ coated dish acquired within 24 hrs of placement of medium into the dish. The marked reduction in meniscus magnitude is evident.

Application of various silicone coatings to polystyrene were shown to greatly reduce, or eliminate the meniscus width and optical interference. One day after treatment of the surfaces, Methocult™ was added to the wells or dishes. Meniscus reduction at this timepoint, as measured by optical interference, ranged from a 50% reduction to >95% reduction of the visible meniscus relative to the untreated control dishes (see FIG. 3—Untreated, FIG. 4—Aquasil™, FIG. 5—Sigmacote™, FIG. 6—Syl-off™, FIG. 7—Surfasil™). Ranking of effectiveness at meniscus reduction of the various coatings was as follows: 1. Syl-off™ 2. Surfasil™ 3. Aquasil™ 4. Sigmacote™.

During 10 days of incubation in a 37° C., 5% $CO_2$, humidified incubator, the measured magnitude of the meniscus was seen to increase within the first 4 days of incubation for Sigmacote™, Surfasil™, and Aquasil™ treated surfaces, but not for Syl-off™ treated surfaces. Syl-off™ treatment with the wipe-on method effectively eliminated the meniscus under all experimental conditions. These results suggest that for many coatings the meniscus reduction effect with Methocult™ is only temporary.

Example 10

Effects of Perfluorocarbon Polymer Coatings on Meniscus Properties

Figure 8:
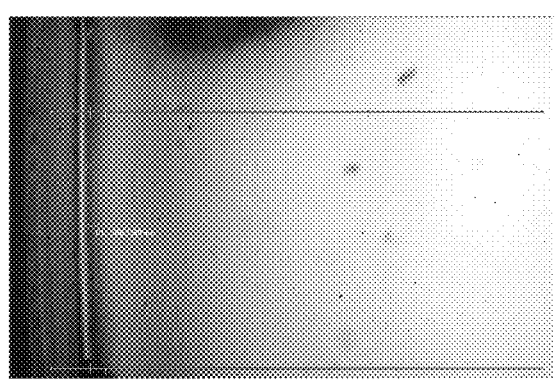
FIG. 8 is an image of the dish wall/culture medium interface of a Fluoropel™ (Cytonix Inc.) coated dish acquired within 24 hrs of placement of medium into the dish. The application of a thin film of this coating material results in a distinct boundary between the dish wall and the culture medium. No significant meniscus is evident.

Polystyrene culture dishes (35 mm Greiner, 627102) were coated with a perfluorocarbon polymer (Fluoropel™, Cytonix Corp.) by the immersion method described in Example 2. Following the perfluorocarbon application, surfaces were allowed to cure for 5 min at 60° C. followed by a >1 hr drying period at ambient temperature and humidity. 1 to 2 mL of MethoCult™ semisolid medium was added to coated culture dishes and allowed to equilibrate for a minimum of 2 hrs at ambient temperatures and humidity, and for a period of 10 days in a 37° C., 5% $CO_2$, humidified incubator. Meniscus properties were quantified as described in Examples 6 and 7. The effect of the perfluorocarbon coating is illustrated in FIG. 8. Meniscus width was greatly reduced with the coating (<0.01 mm, as compared to 2.4 mm for untreated dishes) and optical interference was diminished to <1% of that of uncoated dishes. The meniscus reducing property of the coating was stable during prolonged incubation, with no further increase in meniscus magnitude noted after a period of 10 days (Table 2).

Example 11

Effects of Paraffin Wax Coatings on Meniscus Properties

Polystyrene culture dishes (35 mm Greiner, 627102) were coated with paraffin wax (3134 melting point). The wax coating was applied by melting paraffin and preheating the culture dish under a stream of heated air. The preheated dish was filled with liquid wax and the excess was decanted from the well. The dish was rotated in the vertical orientation allowing the wax to solidify in an even coating with cooling of the dish. Excess wax was removed from the bottom of the dish using a cell lift scraper.

Figure 9:
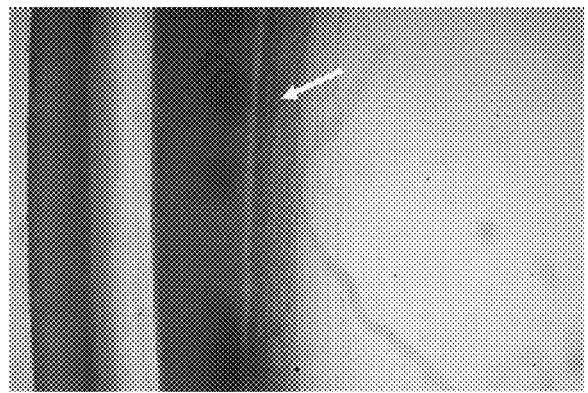
FIG. 9 is an image of the dish wall/culture medium interface of a paraffin coated dish acquired within 24 hrs of placement of medium into the dish. The paraffin coating is visible as an opaque area with a light boundary (arrow) facing the interior of the well. A slight meniscus is evident as a faint darkened area adjacent to the paraffin coating.

2 mL of MethoCult™ semisolid medium was added to the wax coated culture dishes and incubated at 37° C. in a humidified incubator. Meniscus properties were quantified after 1, 4, and 10 days of incubation as described in Examples 6 and 7. The effect of the wax coating is illustrated in FIG. 9. Meniscus width was greatly reduced with Paraffin coating (0.33 mm, as compared to 2.1 mm for untreated dishes) and optical interference was diminished to approximately 10% of that of uncoated dishes. The measured magnitude of the meniscus was seen to increase within the first 4 days of incubation and stabilized at approximately half of the magnitude of uncoated dishes by day 10 (Table 2).

Example 12

Effects of Petrolatum Coatings on Meniscus Properties

Figure 10:
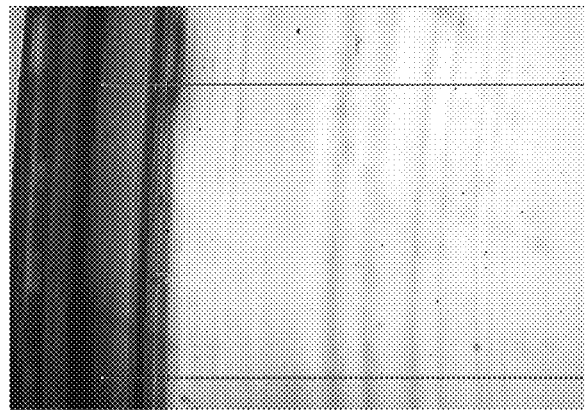
FIG. 10 is an image of the dish wall/culture medium interface of a petrolatum coated dish acquired within 24 hrs of placement of medium into the dish. The translucent petrolatum coating is visible on the culture surface of the dish as an area of undulating intensity. No significant meniscus is evident.

Polystyrene culture dishes (35 mm Greiner, 627102) were coated with a petroleum jelly (100% white petrolatum, USP) by the wipe-on/wipe-off method described in Example 1. Following the application, surfaces were allowed to cure for 30 min at 70° C. 1 to 2 mL of MethoCult™ semisolid medium was added to coated culture dishes and allowed to equilibrate for a minimum of 2 hrs at ambient temperatures and humidity. Meniscus properties were quantified as described in Examples 6 and 7. The effect of the petrolatum coating is illustrated in FIG. 10. Meniscus width was greatly reduced with the coating (<0.01 mm, as compared to 2.4 mm for untreated dishes) and optical interference was diminished to <1% of that of uncoated dishes (Table 2).

Example 13

Static and Dynamic Contact Angles of Polymeric Solid Surfaces and the Effect of Perfluorocarbon and Siloxane Coatings Advancing and receding contact angles were measured as described in Example 4 for several polymeric solid surfaces coated with either siloxane (Syl-off™, Dow Corning) or fluoropolymer (Fluoropel™, Cytonix Inc.) coating agents, or left untreated. The siloxane coating was applied by the wipe-on method described in Example 1 whereas the fluoropolymer coating was applied by the immersion method described in Example 2. Surfaces evaluated included polystyrene (PS), polytetrafluoroethylene (PTFE), polypropylene (PP), polyvinylchloride (PVC), polyetheretherketon (PEEK), and high-strength silicone rubber sheeting (McMaster). Contact angles were measured with water, and several aqueous solutions including Iscove's Modified Dulbecco's Medium (IMDM), IMDM containing either 0.26%, 1%, or 2.6% methylcellulose, phosphate buffered saline (PBS), and PBS containing 2% fetal bovine serum (PBS+2% FBS). The complete results are summarized in Table 3 which shows static contact angle (CA) and dynamic minimum contact angles (DM CA) of various treated and untreated surfaces with differing aqueous solutions. Conditions where contact angles permissive for meniscus elimination are obtained have been highlighted.

Untreated polymeric plastic solid surfaces tend to exhibit static contact angles between 85 to 105 degrees with the majority of aqueous solutions tested. Similarly, cross-linked siloxane polymers (high-strength silicone rubber, McMaster) tend to exhibit static contact angles of approximately 90 degrees with the range of aqueous solutions tested. However, untreated plastic and silicone rubber surfaces exhibited a wide range of dynamic minimum (receding) contact angles dependent on the properties of the aqueous solution. Water and simple ionic aqueous solutions (PBS, IMDM) tended to form dynamic minimum (receding) angles in the range of 90 to 105 degrees. In contrast, dynamic minimum (receding) contact angles of untreated surfaces were less than 85 degrees for viscous aqueous solutions (containing 0.26% to 2.6% methylcellulose) or solutions containing macromolecules such as proteins (PBS containing 2% fetal bovine serum).

A thin-film fluoropolymer coating (Fluoropel™, Cytonix Inc.) of smooth polymeric (PS, PP, PTFE, PEEK, PVC) and high-strength silicone rubber surfaces effectively increases the dynamic minimum contact angle to between 85 and 105 degrees. Similarly, a thin-film coating of non-crosslinked siloxanes (Syl-off™, Dow Corning) on these surfaces effectively increases the dynamic minimum contact angle to above 85 degrees.

Example 14

Meniscus Properties with Polymeric Surfaces in Dynamic as Compared to Static Systems Meniscus properties were examined in untreated or fluoropolymer coated 35 mm culture dishes (Greiner 627102), and 35 mm culture dishes containing either untreated or siloxane coated PTFE inserts, untreated, siloxane, or fluoropolymer coated PEEK inserts, and fluoropolymer coated PVC inserts. Fluoropolymer coatings (Fluoropel™, Cytonix Inc) were applied to the surfaces by the immersion method (Example 2), and non-crosslinked siloxane coatings (Syl-off™, Dow Corning) were applied by the wipe-on method (Example 1). A volume of aqueous solutions sufficient to result in a liquid level of approximately 2 to 3 mm within the culture dishes was added. For static meniscus measurements, the liquid was gradually added to the center of the dish until the liquid level on the dish wall had advanced to a height of approximately 2 mm. All static measurements were completed without any physical disturbance to the dish. Dynamic meniscus measurements were conducted after the dishes were rotated to advance the liquid level up and down the wall surface of the dish. Meniscus measurements were conducted immediately after liquid additions, and again after a nine day static incubation. Meniscus width and height measurements were completed by the methods described in Example 6. Optical interference imparted by the meniscus was determined by the method described in Example 7. The results are summarized in Table 4 which shows meniscus formation for various treated and untreated surfaces with differing aqueous solutions with static and dynamic environments, and after a nine day incubation. Meniscus magnitude is given in terms of width (mm) and optical interference. Conditions where significant meniscus reduction is observed are highlighted. Meniscus reducing effects of surface coatings are maintained throughout the nine-day incubation period.

The untreated and not previously wetted polymeric surfaces tend to exhibit no significant meniscus with the tested aqueous solutions in the static system. In addition, no significant meniscus is imparted by dynamic manipulation of the untreated surfaces when the aqueous liquid is water or a simple ionic aqueous solution (IMDM). However, with viscous aqueous solutions (1% methylcellulose/IMDM), or protein containing solutions (PBS+2% FBS), a significant meniscus is imparted by dynamic manipulation of the dishes containing untreated polymeric surfaces.

A thin-film fluoropolymer coating (Fluoropel™, Cytonix Inc) of PS, PEEK, or PVC wall surfaces of culture dishes effectively eliminated the meniscus observed with the tested viscous and protein containing aqueous solutions in the dynamic system. Likewise, a thin-film coating of PTFE or PEEK inserts with non-crosslinked siloxanes (Syl-off™, Dow Corning) effectively prevented formation of a significant meniscus with the tested viscous and protein containing aqueous solutions (1% methycellulose/IMDM and PBS+2% FBS). These meniscus properties of treated and untreated surfaces were stably maintained during a nine day static incubation (Table 4).

Example 15

Relation Between Meniscus Magnitude and Static and Dynamic Minimum Contact Angles Taking into consideration the data presented in Examples 13 and 14, a correlation between contact angles and meniscus magnitude was established. The relationships are presented in FIGS. 11a and 11b. Graph 11a shows the relation between contact angles measured for all conditions and their corresponding meniscus magnitude (as indicated by optical interference). In this graph, static and dynamic contact angle measurements are paired with the corresponding static and dynamic meniscus magnitude. In graph 11b, the dark circles depict the static contact angles measured for untreated surfaces and their resulting dynamic meniscus magnitude (as indicated by the optical interference). The open squares represent the relation between dynamic contact angles and their resulting dynamic meniscus magnitude.

Figure 11:
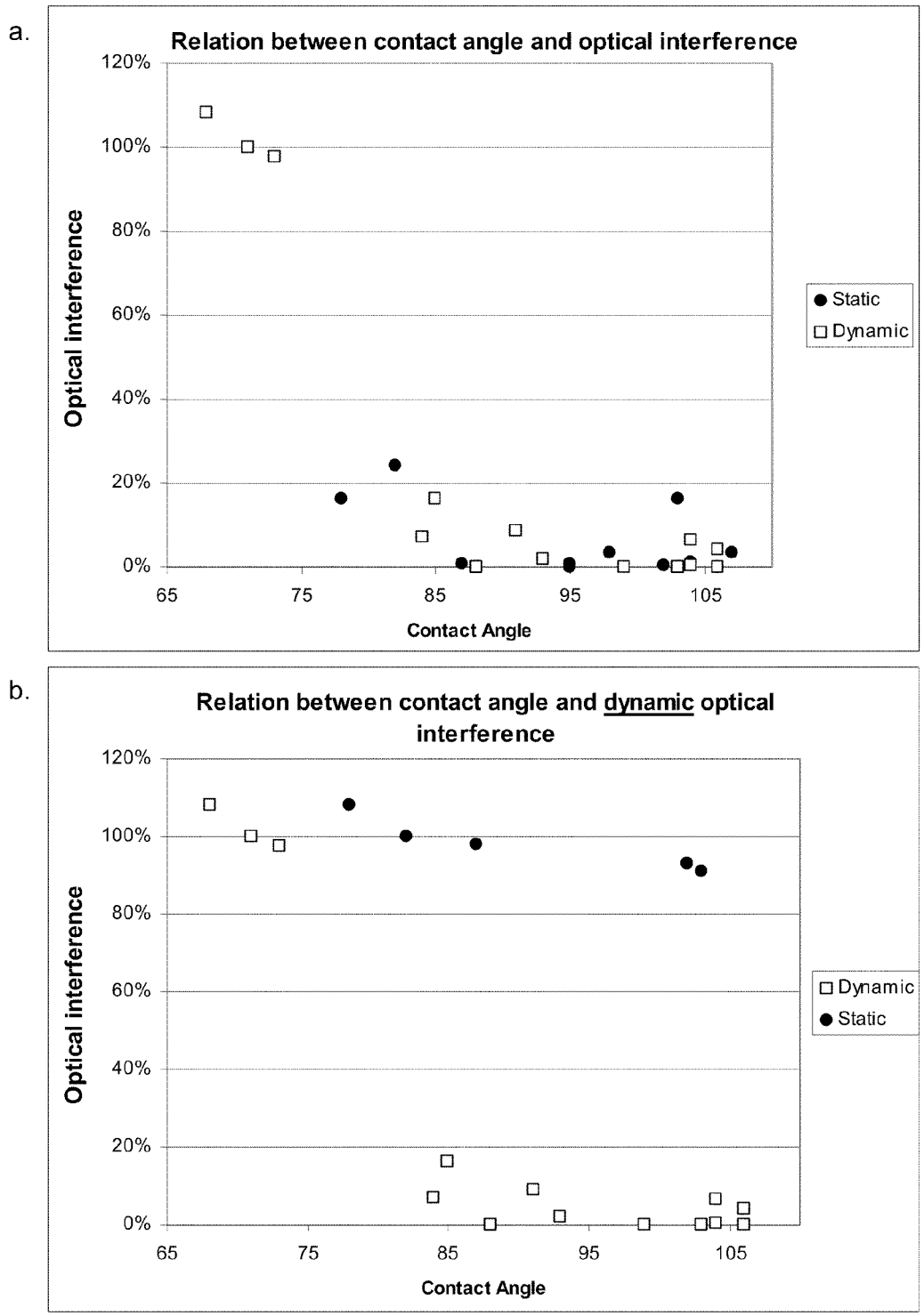
FIG. 11 shows the correlation between dynamic meniscus magnitude and static and dynamic minimum contact angles. Meniscus magnitude is given in terms of optical interference relative to that of untreated polystyrene control dishes containing 1% methylcellulose/IMDM. Panel "a" shows the relation between contact angles measured for all conditions and their corresponding meniscus magnitude. Panel "b" shows the relationships between the static contact angle of untreated polymeric surfaces and the resulting dynamic meniscus magnitude (closed circles). This is compared to the relationship between dynamic minimum contact angle and the resulting dynamic meniscus magnitude (open squares).
Figure 12:
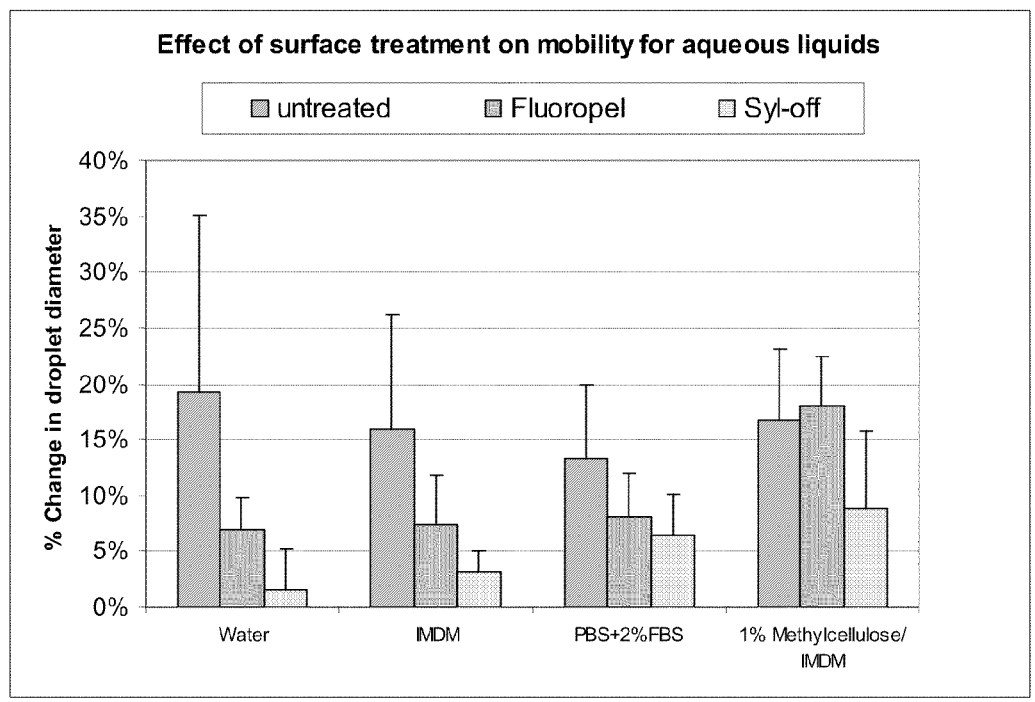
FIG. 12 shows the effect of fluoropolymer and siloxane treatment of polymeric surfaces on surface mobility of aqueous solutions. Mobility is increased with non-crosslinked siloxane treatment and fluoropolymer treatment. The increase in mobility is diminished with viscosity of the liquid (1% methylcellulose).

Contact angles in the range of 75 to 110 degrees resulted in negligible or no significant meniscus under the same physical conditions (static or dynamic). Contact angles below 75 degrees caused formation of a meniscus with significant optical interference (FIG. 11a). Contact angles of approximately 110 degrees and greater, resulted in a convex meniscus (visual observation) which is manifested as a slight increase in optical interference. FIG. 11a also illustrates that the static contact angles for most polymeric surfaces with aqueous solutions are greater than 85 degrees, whereas contact angles less than 85 degrees are primarily observed under dynamic conditions.

Dynamic minimum contact angles in the range of 75 to 110 degrees resulted in no significant meniscus. This correlation between dynamic minimum contact angles and meniscus magnitude is maintained in both static and dynamic systems. This is evident in FIGS. 11a and 11b. In dynamic conditions (open squares), contact angles between approximately 85 and 105 degrees resulted in an optical interference of less than 20%. However, there is no relation between static contact angles and meniscus magnitude for untreated polymeric surfaces (closed circles) and static contact angles between approximately 75 and 105 degrees resulted in a meniscus with an optical interference of approximately 100% (FIG. 11b).

These correlations confirm that a dynamic minimum contact angles in the range of 75 to 110 degrees are required for significant meniscus reduction, whereas a static contact angle within this range is ineffective in preventing meniscus formation with dynamic manipulation of the culture dishes for viscous or protein containing aqueous solutions.

Example 16

Effect of Surface Treatments on Mobility with Aqueous Solutions

Surface mobility was determined as described in Example 12, and is given as the degree of change in the droplet diameter after a cycle of advancing and receding the droplet perimeter by volume change. The percent change in droplet diameter for surfaces with fluoropolymer and siloxane coatings are shown for different aqueous solutions in FIG. 35. Fluoropolymer coatings (Fluoropel™, Cytonix Inc) were applied to surfaces by the immersion method described in Example 2, and siloxane coatings (Syl-off™, Dow Corning) were applied by the wipe-on method described in Example 1. The values in the graph are the averages of observed mobility across several polymeric surfaces, including polystyrene, polypropylene, polyvinylchloride, polyetherketone, and polytetrafluoroethylene, with or without the above coatings.

While variability is observed for mobility depending on the polymeric substrate, on average, the degree of change in the droplet diameter is somewhat reduced with the fluoropolymer coating, and significantly reduced with the siloxane coating. The difference in mobility between treated and untreated surfaces was greatest for water and IMDM, for which very high mobility was observed with siloxane and fluoropolymer coatings. Addition of protein (2% FBS) or an increase in viscosity (1% methylcellulose) reduced the mobility of the coated surfaces, although the siloxane coating retained a significantly higher mobility than the untreated surface. The improved mobility of coated surfaces with viscous and protein containing solutions is thought to enhance the meniscus diminishing effect by enabling a return of the three-phase contact line to its equilibrium with minimum energy input. Thus, surfaces with high mobility may allow the force of gravity and surface energies to rapidly return the solid-liquid-vapor contact line to approach its equilibrium contact angle, thereby diminishing the meniscus formed by dynamic disturbance of the liquid level.

Example 17

Figure 13:
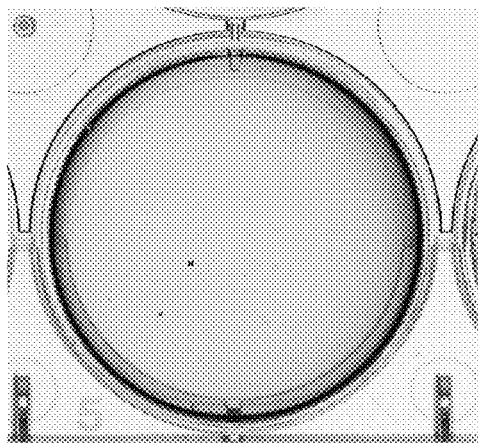
FIG. 13 is an image acquired using Gelcount of tissue culture treated 6-well plate shows a darkened circle around circumference when filled with 1.1 mL of MethoCult™. The well is about 36 mm across.
Figure 14:
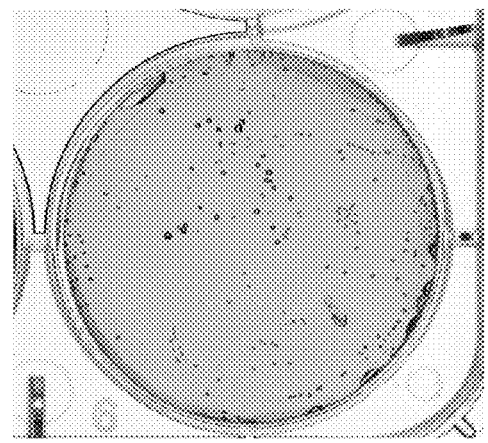
FIG. 14 is an image acquired using Gelcount of well containing MethoCult™ where the wall coated with silicone sealant does not show the same dark edge around most of the circumference. The many round spots in the medium are bubbles that were introduced in handling the MethoCult™ prior to addition to the well. The well is about 36 mm across.

Effect of Silicone Coating of Well Walls on Images Acquired by Transmission Light Scanning A layer of silicone sealant (Dow Corning) was applied to the walls of a well in a standard 6-well tissue culture treated plate (Corning, #3516). About 1.5 mL of methylcellulose-based cell culture media (MethoCult™ 4434, Stemcell Technologies, Canada) was added to each well. The meniscus was noticeably less pronounced in the well with the wall coated with silicone. Images of wells without (FIG. 13) and with (FIG. 14) the hydrophobic silicone coating were acquired using a scanning device (Gelcount, Oxford Optronix, England). The well without the coating has a dark rim around the edge due to refraction by the meniscus of the methycellulose medium, whereas the wells with the hydrophobic coating show a negligible effect at the edge. Under typical conditions it is more difficult to distinguish the colonies near the rim of the dish because of the effect of the meniscus.

Example 18

Figure 15:
FIG. 15 is an image acquired using an inverted microscope of the edge of a well coated with silicone in the same 24-well plate as seen in FIG. 16. The image shows a much smaller band of darkness at the well wall (left side of picture). The exposure and illumination settings where the same as for the image in FIG. 16. The jagged vertical line in the center of the image shows where there is a thickened silicone coating resulting from the application method. The center of the well is not coated.
Figure 16:
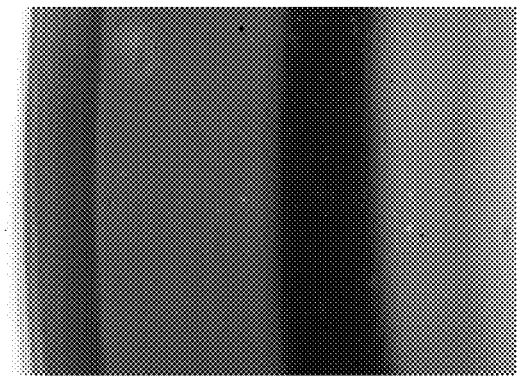
FIG. 16 is an image acquired using an inverted microscope of the edge of a well in an untreated 24-well plate. The image shows a darkened area extending from the well wall at left into the center of the well (right side of image). The image is approximately 1.3 mm across.
Figure 17:
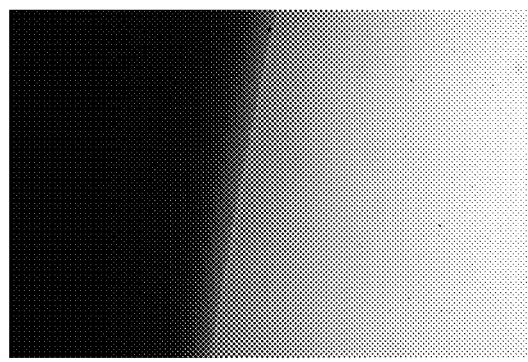
FIG. 17 is an image of a well with Buna nitrile rod seal (026-70D) insert, filled with 1 mL of MethoCult™. There is a clear boundary between the edge of the seal and the medium (indicated by the dashed line).
Figure 18:
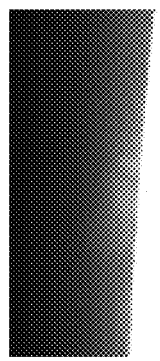
FIG. 18 is an image of a well with Buna nitrile rod seal (025-70D) insert, filled with 1 mL of MethoCult™. There is a clear boundary between the edge of the seal and the medium (indicated by the dashed line).
Figure 19:
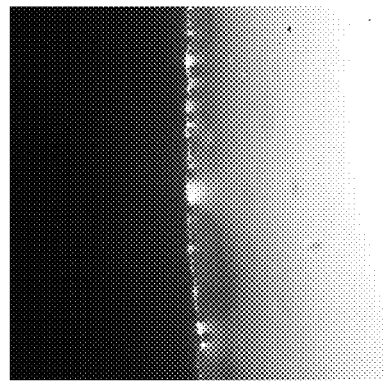
FIG. 19 is an image of a well with an FDA approved silicon o-ring (#123) insert, filled with 1 mL of MethoCult™. There is a clear boundary between the edge of the seal and the medium (indicated by the dashed line). The speckling at the boundary is likely due to slight differences in the wetting of the silicon ring that create small meniscus effects.
Figure 20:
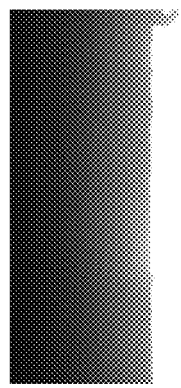
FIG. 20 is an image of a well with an FDA approved EPDM (70D-026) insert, filled with 1 mL of MethoCult™. There is a clear boundary between the edge of the seal and the medium (indicated by the dashed line).
Figure 21:
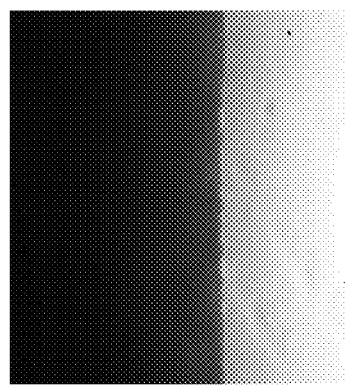
FIG. 21 is an image of a well with an FDA approved EPDM (70D-025) insert, filled with 1 mL of MethoCult™. There is a clear boundary between the edge of the seal and the medium (indicated by the dashed line).

Effect of Silicone Coating of Well Walls on Images Acquired by Transmission Light Microscopy A layer of silicone sealant (Dow Corning Silastic Type A #3233880-1101) was applied to the walls of all wells in columns 4, 5 and 6 in a 24-well non-treated tissue culture plate (Corning) using a cell scrapper (Falcon). A relatively thin layer of silicone was applied to the walls, but in doing so some silicone sealant adhered to the bottom of the well, creating a ring. The ring is visible as a jagged vertical line in the middle of FIG. 15. 250 µL of MethoCult™ was added to coated and uncoated wells on the same plate. When viewed using brightfield microscopy on an Axiovert 40 CFL (Zeiss), there is a clear difference in the darkening effect of the meniscus at the edge of the wells between the coated and uncoated wells. Images taken using a Fuji Finepix™ S2 set at a $\frac{1}{8}^{th}$ s exposure with constant condenser illumination through a 5× magnification objective and 2.5× camera ocular are shown in FIG. 15 and FIG. 16. The optical effect of the meniscus on the light reaching the camera is markedly different for the wells that are coated with a hydrophobic silicone layer and those that are not. In the wells with no silicone coating the reduction in the light intensity extends at least 1.3 mm from the wall of the well (FIG. 16). The optical effect seen in the uncoated well interferes with the counting and identification of colonies grown in MethoCult™.

Example 19

Figure 22:
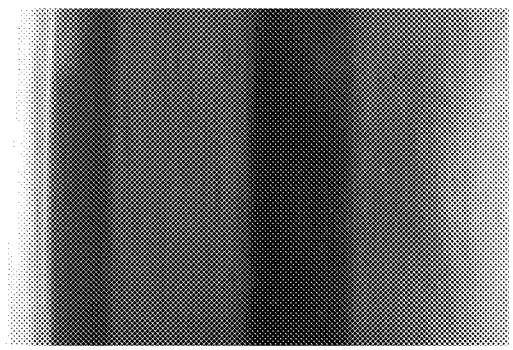
FIG. 22 is an image of a well with no insert, filled with 1 mL of MethoCult™. The boundary between the well wall and the medium (indicated by the dashed line) is not clear and there is a region of variable shading in the medium that is detrimental to colony counting.

Effect of Different Wall Materials on Images Acquired by Transmission Light Microscopy To examine the effect of different wall materials on the meniscus, rings (Able O-Rings and Seals) of silicon, EPDM, and buna nitrile, which are hydrophobic materials, were placed into the wells of a tissue culture treated 6-well plate (Corning Catalog #3516). The rings had outer diameters close to that of the inner diameter of the wells. 1 mL of MethoCult™ (#4434) was then added. All the rings reduced the meniscus and essentially eliminated the dark region typically seen at the circumference of the well. Images were taken at the inner edge of the ring or well using the same method and equipment as described in FIG. 14. FIG. 17 through FIG. 21 show images taken at the edge of the wells containing MethoCult™ with the rings in place. The rings appear as a curved dark line on the left of the images. The image brightness for all the wells with rings is relatively uniform when compared to the image brightness for the well with no ring insert shown in FIG. 22. There were two wells where the rings lifted off the bottom at various points around the circumference of the well. This resulted in a less distinct boundary between the wall and the medium. After the rings were pushed back down the boundary became distinct again.

The rings all create a clear image of the media right up to the ring wall. The boundary between the wall and the medium is very distinct, more so than when the well wall is coated using the silicone sealant as in Example 17 and Example 18. This improvement may be due in part to the light absorbing properties of these materials. The ring materials suppress any light reflected or refracted by the clear plastic of the well wall.

Example 20

Effect of Siloxane Polymer Coatings on Meniscus Properties in Various Multiwell Plate Formats Meniscus magnitude is maintained in untreated polystyrene culture wells of various diameters. As a result, in smaller culture wells, the proportional optical interference due to the meniscus is increased. For example, in 6 well plates containing MethoCult™ medium, the meniscus covers approximately 23% of the well surface area. By comparison, in 96 well plates the meniscus covers 83% of the well surface leaving only the center of the well available for unhindered microscopic analysis. Meniscus reduction in various multiwell plate formats has broad ranging applications. In this example, 24 and 96 well polystyrene culture plates (Costar 3473 and 3370) were coated with various siliconizing agents. Sigmacote™ (Sigma SL2) was applied by partially filling wells with the agent and allowing a contact time with the polystyrene surfaces for a period of ~10 min, then aspirating the excess agent and air drying the residual solvent. Syl-off™ (Dow Corning Q2-7785) and Surfasil™ (Pierce 42800) were applied by partially filling wells with the agent and allowing a contact time with the polystyrene surfaces for a period of ~10 min. Excess agent was removed by aspirating into a pipet and wiping the culture wells with a lint-free tissue. Residual solvent was evaporated by air drying. Silicone coatings were cured by incubation at 72° C. in a drying oven for a period of 3 hrs. 50 and 150 µL of MethoCult™ (Stemcell Technologies H4434) were placed into the 24 and 96 well plates respectively. After a 30 min equilibration period at ambient conditions, meniscus magnitude (width and optical interference) was quantified as described in Examples 6 and 7.

Figure 23:
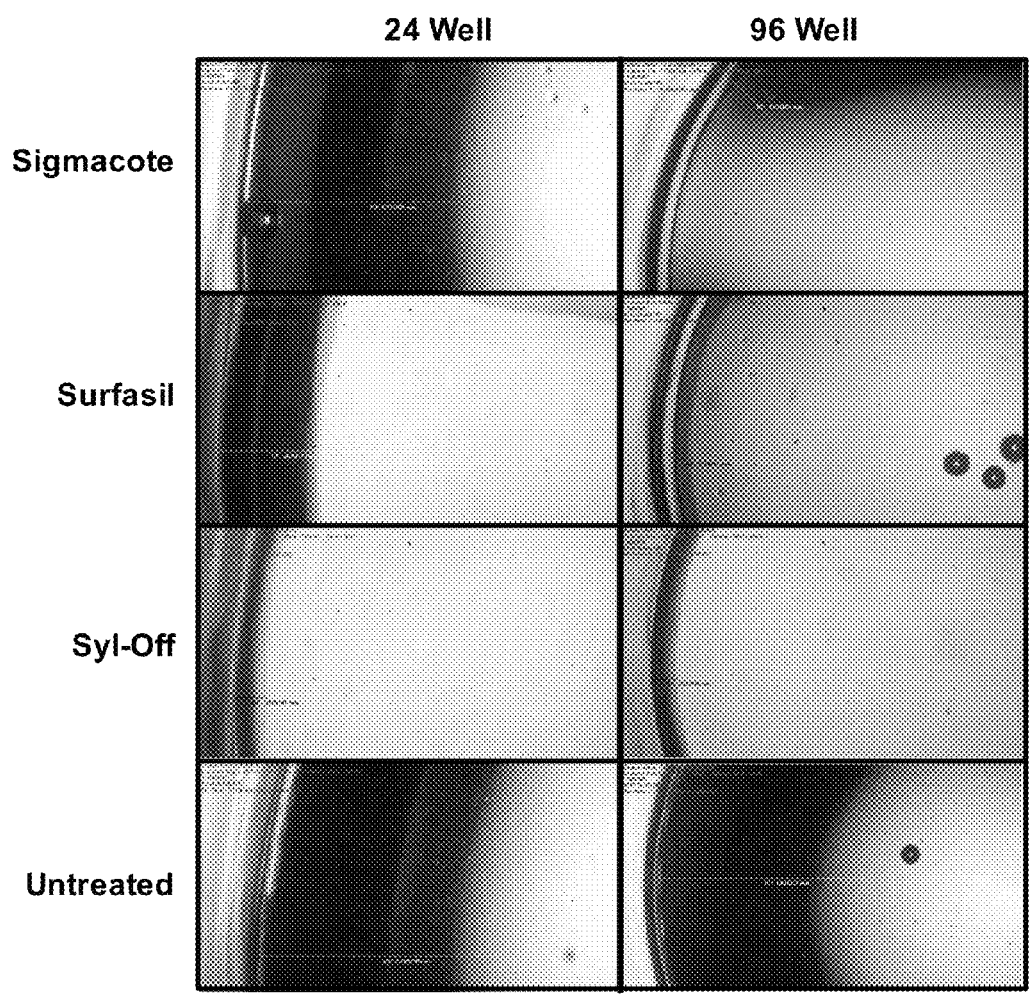
FIG. 23 are images the dish wall/culture medium interface of wells of 24 and 96 well culture plates untreated, or treated with Sigmacote™, Surfasil™, and Syl-off™. The effectiveness of Syl-off™ and Surfasil™ treatments in achieving meniscus reduction in wells of reduced diameter is demonstrated, while a meniscus of varying magnitude is seen for Sigmacote™ treatments.
Figure 24:
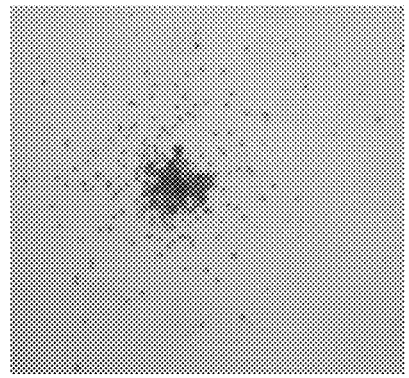
FIG. 24 is a photograph showing compact granulocyte colony (CFU-G) before addition of Neutral Red Stain.
Figure 25:
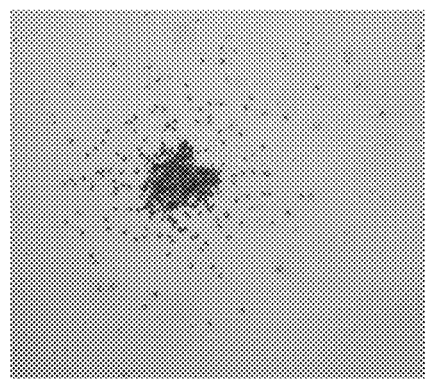
FIG. 25 is a photograph showing compact granulocyte colony (CFU-G) after addition of Neutral Red Stain.

The effect of silicone coatings is summarized in Table 5. The Syl-off™ and Surfasil™ silicone treatments are shown to significantly reduce meniscus magnitude in all cases. This is illustrated in FIG. 25. Syl-off™ is shown to nearly eliminate the meniscus and is the preferred treatment. Sigmacote™ treatment with the stated method of application did not appreciably diminish the meniscus and a significant optical interference remains. In the 96 well plate format, Sigmacote™ treatment resulted in uneven meniscus reduction around the perimeter of the well (FIG. 23). This treatment may be effective with further development of the application method.

Example 21

Aerosol Delivery of Stain to Colonies and Effect on Colony Contrast with Background The stain Neutral Red (Sigma, Mo.) was applied as an aerosol to colonies growing in MethoCult™ plated in 35 mm dishes (Greiner 627102), 6-well plates or 24-well plates (Corning) using a commercial nebuliser designed to deliver drugs (Inspiration™ Respironics Model 626 Compressor Nebulizer). At least 2 mL of the solution (0.2% w/v of stain) was pipetted into the nebulising chamber. The nebuliser aerosolized the stain, which was carried in an air stream through a length of tubing to the culture dishes (Tygon). The open end of the tubing was held over each dish or well to direct the aerosol towards the surface of the culture medium. The duration of application for each well or dish depended on the surface area and the desired intensity of staining. For a 35 mm dish or well in a 6-well plate, applying the stain for 1 min produced the greatest increase in contrast as judged qualitatively by looking under the microscope before and after application. For wells in a 24-well plate, about 20 s was used. The dye was applied evenly by moving the tubing around above the surface of the well or plate. The stain was incubated for 20 minutes before inspecting the colonies by light microscopy.

Figure 26:
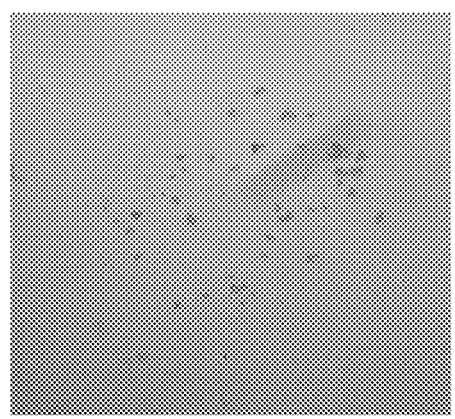
FIG. 26 is a photograph showing dispersed granulocyte colony (CFU-G) before addition of Neutral Red Stain.
Figure 27:
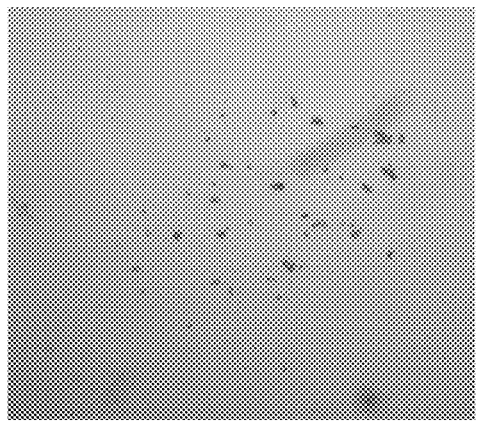
FIG. 27 is a photograph showing dispersed granulocyte colony (CFU-G) after addition of Neutral Red Stain.
Figure 28:
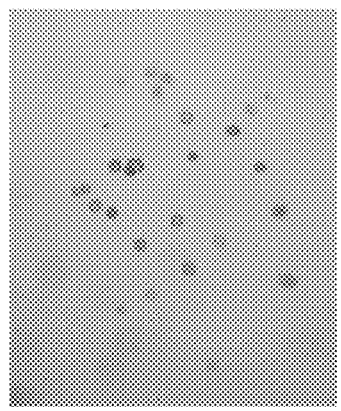
FIG. 28 is a photograph showing dispersed macrophage colony (CFU-M) before addition of Neutral Red Stain.
Figure 29:
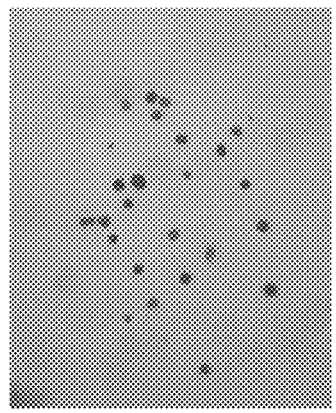
FIG. 29 is a photograph showing dispersed macrophage colony (CFU-M) after addition of Neutral Red Stain.

By aerosolizing the stain, it is distributed more evenly and at a slower rate than when added with a pipette. This allows the colonies to be stained without disturbing the colony morphology appreciably. The photos in FIG. 24 to FIG. 29 were taken using an inverted light microscope in transmission mode and show myeloid colonies before and after addition of stain. The digital photographs were not manipulated other than to adjust the background intensity to a similar level to allow better comparison between the treated and untreated colonies. The individual cells stand out more clearly and have sharper borders with the stain (FIG. 25, FIG. 27, and FIG. 29). Although there are subtle changes in the relative position of some cells and cell aggregates, particularly between FIG. 26 and FIG. 31, the addition of the stain has not changed the overall colony shape and in each case they are recognizable as the same colony before and after addition of the stain.

Although a common dye that stains lysosomes was used, other staining reagents that work without permeabilizing the cell membrane could be used such as immuno fluorescent stains targeting cell surface markers or vital dyes that stain intracellularly such as calcein AM, calcein red-orange AM, Lavacell (Active Motif, CA), Cell Trace™ BODIPY™ TR methyl ester, LysoTracker Red DND-99, Heochst 33342, TubulinTracker Green, ER-Tracker Red, Nile blue, Nile red and Bismarck brown.

Example 22

Specific Staining of Subclasses of Hematopoetic Progenitor Cells Using Immuno-fluorescent Stains and Fluorescent Intracellular Metabolic Intermediates Fluorescently labeled antibodies to cell surface markers on hematopoetic progenitor cells are generated by conjugation of fluorescein isothiocyanate (FITC) and are commercially available from various sources. An antibody to a cell surface marker on erythroid cells (mouse anti-human anti-glycophorinA, Stemcell Technologies 10423) was diluted to concentrations between 20 and 70 µg/mL in PBS and this solution was applied to a 35 mm cell culture dish (Greiner 627102) containing mature colonies of human hematopoetic progenitor cells by spraying onto the surface of the culture medium. The label was sprayed by feeding the antibody solution to an airbrush gun (KopyKake C3000GV) at a constant rate using a peristaltic pump (Rainin, model RP-1) resulting in a constant and even spray pattern from the airbrush nozzle. The spray was directed at the culture surface until the entire volume of stain—typically between 200 and 300 µL of solution (containing 4 to 20 µg of labeled antibody) of the solution was applied. As with the nebulizer delivery of stain described in Example 21, delivering the stain with the airbrush did not disturb the colony morphology appreciably. After application of the fluorescent stain, the culture dish was incubated in a 37° C., 5% $CO_2$, humidified incubator for a period of approximately 18 hrs.

Darkfield and fluorescent Images of the stained dish were acquired using a Lumenera Infinity 2-3 camera attached to a Meiji macrozoom lens set to 0.9× magnification. Illumination was provided by a darkfield light source (Meiji Techno PBH) and sequential images of adjacent fields covering the entire culture dish were obtained with the use of an automated stage (Maerzhauser, Germany). Individual images were tiled using image processing software (ImagePro™, MediaCybernetics) to constitute a single image of the entire dish. FITC excitation was achieved with the use of a blue LED light source (Luxeon Lumineds) and excitation (Chroma, HQ470/40x) and a dual bandpass emission filters (Chroma 59004m).

Figure 30:
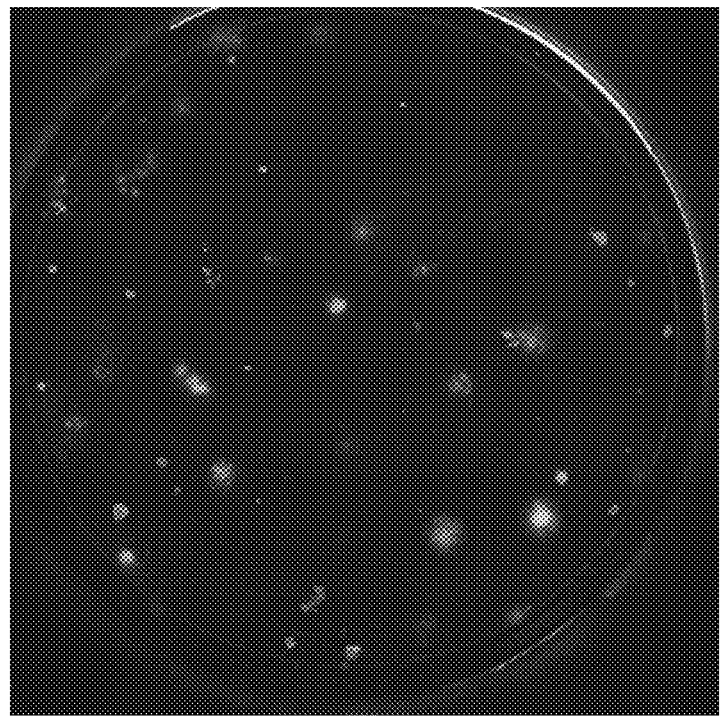
FIG. 30 is a darkfield image of a 35 mm dish exhibiting colonies of hematopoetic cells cultured in Methocult™ semi-solid medium. Sequential adjacent images were acquired with a Lumenera digital camera attached to a macrozoom lens positioned over the culture dish. The acquired images were tiled to constitute a composite image encompassing the entire dish. Colonies of various subclasses are distinguishable.
Figure 31:
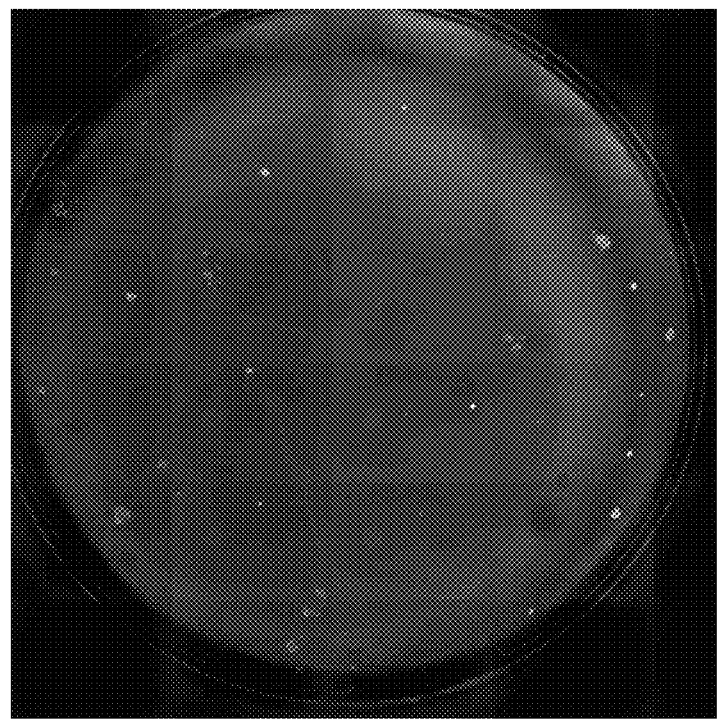
FIG. 31 is a fluorescent image of the dish depicted in FIG. 30. Erythroid colonies were labeled using an antibody to a cell surface marker conjugated to FITC. The green fluorescent background is the result of residual unbound detecting antibody diffused throughout the medium. Brightness and contrast were adjusted to enhance visibility of the stained colonies.

The darkfield image shown in FIG. 30 exhibits a number of clearly defined colonies of various classes of hematopoetic progenitor cells. The corresponding FITC stained dish is shown in the same orientation (FIG. 31). The FITC labeled colonies are sufficiently contrasted from the background to be clearly distinguished, whereas larger unlabeled colonies appear as dark areas and are silhouetted against the dim green background. Thus, this labeling method is suitable for segregation of various colony types by digital image analysis. For example, labeled colonies can be detected, enumerated and analyzed for various physical and optical characteristics using digital image processing software.

An alternate method of applying the stain in a fine mist would be using ink jet technology as embodied in common inkjet printers. The stain could be loaded into the ink cartridge and the printer could "print" the dye onto the wells in an even and well defined way with darker printing equivalent to higher volume addition. Aerosols are also formed in useful volumes by perfume nebulisers.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Treatment | Surface polymer | Meniscus width (mm) Methocult | optical interference Methocult | Advancing Contact angle (°) Methocult | Advancing Contact angle (°) Water | Meniscus Height (mm) |
|---|---|---|---|---|---|---|
| AquaSil ™ | polystyrene | 1.38 | 40% | | | 0.59 |
| SigmaCote ™ | polystyrene | 1.95 | 65% | 83 | 95 | 0.66 |
| Syl-off ™ | polystyrene | 0.09 | 3% | 98 | 105 | <0.2 |
| Surfasil ™ | polystyrene | 1.28 | 47% | 63 | 88 | <0.2 |
| Paraffin | polystyrene | 0.96 | 46% | | | 0.59 |
| untreated | PTFE | 2.42 | 80% | 105 | 104 | |
| Sigmacote | PTFE | 0.41 | 9% | 88 | 95 | |
| Untreated | polystyrene | 2.43 | 100% | 86 | 97 | |

TABLE 2

| Treatment | Measured Meniscus width (mm) Day 1 | Day 4 | Day 10 | Optical interference (% of untreated) Day 1 | Day 4 | Day 10 |
|---|---|---|---|---|---|---|
| AquaSil ™ | 0.60 | 1.17 | 1.38 | 13% | 48% | 40% |
| SigmaCote ™ | 0.60 | 1.88 | 1.95 | 24% | 81% | 65% |
| Syl-off ™ | 0.21 | 0.10 | 0.04 | 3% | 2% | 1% |
| Surfasil ™ | 0.35 | | 1.28 | 18% | | 47% |
| Paraffin ™ | .33 | 1.16 | 0.96 | 10% | 50% | 46% |
| Petrolatum ™ | .05 | | | <1% | | |
| Fluoropel ™ | 0.03 | | 0.04 | <1% | | <1% |
| Untreated control | | | 2.43 | | | 100% |

TABLE 3

| Liquid | Surface | Untreated Static CA | Untreated DM CA | PFC604AFA ™ Static CA | PFC604AFA ™ DM CA | Syl-off ™ Static CA | Syl-off ™ DM CA |
|---|---|---|---|---|---|---|---|
| DI water | PEEK | 90 | 74 | 108 | 107 | 106 | 103 |
| | PP | 86 | 76 | 99 | 91 | 103 | 101 |
| | PS | 92 | 88 | 109 | 103 | — | — |
| | PTFE | 105 | 91 | — | — | 109 | 106 |
| | PVC | 85 | 78 | 111 | 106 | 110 | 110 |
| | silicone | 92 | 76 | — | 111 | 98 | 97 |
| IMDM | PEEK | 99 | 89 | 112 | 107 | 105 | 104 |
| | PP | 91 | 74 | 102 | 96 | — | — |
| | PS | 88 | 88 | 106 | 103 | — | — |
| | PTFE | 107 | 99 | — | — | 104 | 104 |
| | PVC | 75 | 61 | 109 | 112 | 104 | 107 |
| PBS | PS | 92 | 92 | 110 | 108 | — | — |
| | PTFE | 105 | 97 | — | — | 109 | 107 |
| PBS + 2% FBS | PEEK | 107 | 95 | 111 | 106 | 99 | 95 |
| | PP | 96 | 89 | — | — | 100 | 93 |
| | PS | 78 | 68 | 106 | 99 | — | — |
| | PTFE | 103 | 92 | — | — | 98 | 93 |
| | PVC | 80 | 71 | 105 | 105 | 104 | 101 |
| | silicone | 93 | 83 | 107 | 98 | 98 | 95 |
| 0.26% Methylcellulose/IMDM | PS | 84 | 77 | 97 | 90 | — | — |
| | PTFE | 97 | 89 | — | — | 106 | 103 |
| 1% Methylcellulose/IMDM | PEEK | 102 | 92 | 95 | 84 | 107 | 104 |
| | PP | 87 | 74 | 80 | 67 | 90 | 84 |
| | PS | 82 | 71 | 95 | 85 | — | — |
| | PTFE | 87 | 73 | — | — | 104 | 106 |
| | PVC | 82 | 78 | 92 | 84 | 106 | 105 |
| | silicone | 90 | 79 | 95 | 81 | 100 | 94 |
| 2.6% Methylcellulose/IMDM | PS | 81 | 71 | 81 | 67 | — | — |
| | PTFE | 79 | 66 | — | — | 93 | 85 |

TABLE 4

| | | | Treatment | | | | | |
|---|---|---|---|---|---|---|---|---|
| | | | untreated | | PFC604AFA ™ | | Syl-off ™ | |
| Liquid | Surface | Condition | Meniscus (mm) | Opt. Interference | Meniscus (mm) | Opt. Interference | Meniscus (mm) | Opt. Interference |
| water | PS | static | — | — | — | — | — | — |
| | | dynamic | 0.0 | 0% | 0.0 | 0% | — | — |
| | | 9 day incubation | 0.0 | 0% | 0.0 | 0% | — | — |
| | PTFE | dynamic | 0.1 | 9% | — | — | 0.1 | 4% |
| | | 9 day incubation | 0.0 | 2% | — | — | 0.0 | 1% |
| IMDM | PS | dynamic | 0.0 | 0% | 0.0 | 0% | — | — |
| | | 9 day incubation | 0.0 | 2% | 0.0 | 2% | — | — |
| | PTFE | dynamic | — | — | — | — | 0.0 | 0% |
| | | 9 day incubation | — | — | — | — | 0.0 | 0% |
| PBS + 2% FBS | PS | static | 0.0 | 16% | 0.0 | 0% | — | — |
| | | dynamic | 2.1 | 108% | 0.0 | 0% | — | — |
| | | 9 day incubation | 1.8 | 94% | 0.0 | 9% | — | — |
| | PTFE | static | 0.3 | 16% | — | — | 0.0 | 3% |
| | | dynamic | 1.7 | 91% | — | — | 0.0 | 2% |
| | | 9 day incubation | 1.8 | 75% | — | — | 0.0 | 0% |
| 1% Methylcell/ IMDM | PEEK | static | 0.0 | 1% | 0.0 | 1% | 0.2 | 4% |
| | | dynamic | 2.0 | 93% | 0.5 | 7% | 0.6 | 6% |
| | PS | static | 0.3 | 24% | 0.0 | 0% | — | — |
| | | dynamic | 2.2 | 100% | 0.4 | 16% | — | — |
| | | 9 day incubation | 2.0 | 96% | 0.8 | 48% | — | — |
| | PTFE | static | 0.0 | 1% | — | — | 0.2 | 1% |
| | | dynamic | 2.0 | 98% | — | — | 0.0 | 0% |
| | | 9 day incubation | 1.9 | 91% | — | — | 0.0 | 0% |
| | PVC | static | — | — | 0.1 | 0% | — | — |
| | | dynamic | — | — | 0.6 | 9% | — | — |

TABLE 5

| | | Treatment | | | |
|---|---|---|---|---|---|
| Well format | Data | Sigmacote ™ | Surfasil ™ | Syl-off ™ | Untreated |
| 24 well | Meniscus width (mm) | 2.11 | 0.83 | 0.27 | 2.13 |
| | Optical interference (% of untreated) | 99% | 31% | 3% | 100% |
| 96 well | Meniscus width (mm) | Variable (uneven) | 0.18 | 0.23 | 1.89 |
| | Optical interference (% of untreated) | | 15% | 5% | 100% |

The invention claimed is:

1. A vessel for holding liquid, the vessel comprising:
a) a bottom wall and a sidewall extending from the bottom wall, the sidewall and bottom wall configured so that the vessel is of integral, one-piece construction;
b) a coating material on the interior of the sidewall;
wherein the bottom wall is free from the coating material and the coating material provides a treated intrinsic contact angle between the coated interior vessel wall and an aqueous liquid within the vessel and a treated receding contact angle between the coated interior vessel wall and the aqueous liquid, the treated receding contact angle being between about 75 degrees to about 110 degrees and being closer to 90 degrees than the treated intrinsic contact angle.

2. The vessel according to claim 1, wherein the coating material is silicone, EPDM, buna nitrile or petroleum jelly.

3. The vessel according to claim 1, wherein the coating material is a fluoropolymer.

4. The vessel according to claim 1, wherein the vessel is a culture dish or well in a multi well plate.

5. The vessel according to claim 1, wherein the liquid is cell culture medium.

6. The vessel according to claim 1, wherein the treated receding contact angle is about 90 degrees.

7. The vessel according to claim 1, wherein the treated receding contact angle is between about 80 degrees and about 110 degrees.

8. The vessel according to claim 1, wherein the treated receding contact angle is between about 85 degrees and about 105 degrees.

9. The vessel according to claim 1, wherein the vessel is circular.

10. The vessel according to claim 1, wherein the vessel has vertical walls and a flat bottom.

11. The vessel according to claim 1, wherein the vessel is optically clear.

12. The vessel according to claim 1, wherein the treated receding contact angle is less than the treated intrinsic contact angle and is equal to or greater than 90 degrees.

13. The vessel according to claim 1, wherein the coating material comprises at least 60% methyl perfluorobutylethyl siloxane, methylhydrogen siloxane, Dimethyl siloxane and methyl vinyl siloxane crosslinked with at least 85% Trimethylsiloxy-terminated Methyl(perfluorobutylethyl) siloxane, Trimethylsiloxy-terminated methylhydrogen siloxane.

14. The vessel according to claim 1, wherein the treated intrinsic contact angle is farther from 90 degrees than an untreated intrinsic contact angle measured between an uncoated interior vessel wall and the aqueous liquid.

15. The vessel according to claim 14, wherein the treated receding contact angle is closer to 90 degrees than an untreated receding contact angle measured between the uncoated interior vessel wall and the aqueous liquid.

16. The vessel according to claim 1, wherein the coated interior vessel wall provides a first treated receding contact angle when first contacted by the aqueous liquid, and once wetted the coated interior vessel wall provides a second treated receding contact angle when subsequently contacted by the aqueous liquid, the second treated receding contact angle being different than the first treated receding contact angle.

17. The vessel according to claim 16, wherein the second treated receding contact angle is closer to 90 degrees than the first treated receding contact angle.

18. The vessel according to claim 1, wherein the coating material is silicone-based.

* * * * *